United States Patent [19]
Heavner et al.

[11] Patent Number: 6,111,065
[45] Date of Patent: Aug. 29, 2000

[54] PEPTIDE INHIBITORS OF INFLAMMATION MEDIATED BY SELECTINS

[75] Inventors: George A. Heavner, Flemington, N.J.; Rodger P. McEver; Jian-Guo Geng, both of Oklahoma City, Okla.; Douglas J. Riexinger, Flemington, N.J.; Marian Kruszynski, West Chester, Pa.; Leon A. Epps, Baltimore, Md.; Miljenko Mervic, King of Prussia, Pa.

[73] Assignees: Centocor, Inc., Malvern, Pa.; The Board of Regents of the University of Oklahoma, Norman, Okla.

[21] Appl. No.: 08/233,221

[22] Filed: Apr. 26, 1994

Related U.S. Application Data

[63] Continuation of application No. 07/809,942, Dec. 18, 1991, abandoned.

[51] Int. Cl.$^7$ .............................. C07K 14/00; C07K 7/04
[52] U.S. Cl. ..................... 530/300; 530/324; 530/325; 530/326; 530/333; 514/2; 435/69.1
[58] Field of Search ............ 435/69.1; 530/300, 530/324, 333, 325, 326; 514/12, 2

[56] References Cited

U.S. PATENT DOCUMENTS

| | | |
|---|---|---|
| 4,391,749 | 7/1983 | Engvall et al. . |
| 4,517,686 | 5/1985 | Ruoslahti et al. . |
| 4,578,079 | 3/1986 | Ruoslahti et al. . |
| 4,579,840 | 4/1986 | Hahn ........................................ 514/14 |
| 4,589,881 | 5/1986 | Pierschbacher et al. . |
| 4,605,644 | 8/1986 | Foker . |
| 4,614,517 | 9/1986 | Ruoslahti et al. . |
| 4,661,111 | 4/1987 | Ruoslahti et al. . |
| 4,686,283 | 8/1987 | Nestor et al. . |
| 4,783,330 | 11/1988 | Furie et al. . |
| 4,789,734 | 12/1988 | Pierschbacher . |
| 4,792,525 | 12/1988 | Ruoslahti et al. . |
| 4,879,237 | 11/1989 | Rudslahti et al. . |
| 5,198,424 | 3/1993 | McEver ..................................... 514/13 |
| 5,464,935 | 11/1995 | Heavner et al. ......................... 530/329 |

FOREIGN PATENT DOCUMENTS

| | | |
|---|---|---|
| 90/05786 | 5/1990 | WIPO . |
| 91/06632 | 5/1991 | WIPO . |
| 91/07993 | 6/1991 | WIPO . |

OTHER PUBLICATIONS

Jacobs et al., Nature, 313, 1985, p. 806 "Isolation and Characterization of Genomic . . . ".
Merrifield et al., J. Am. Chem. Soc., 85, p. 2149, 1963, "Solid Phase Peptide Synthesis . . . ".
Johnston et al. Cloning of GMP–140 . . . Cell 56 : 1033–1044 1989.
Beckstead, J.H, et al., "Immunohistochemical Localization of Membrane and α–Granule Proteins in Human Megakaryocytes: Application to Plastic–Embedded Bone Marrow Biopsy Specimens," *Blood*, vol. 67, No. 2 pp. 285–293, (Feb., 1986).
Berkow, R., editor, The Merck Manual of Diagnosis and Therapy, 14th Edition, pp. 649, 2404, 2405 (1982).
Bevilacqua, M.P., et al., "Endothelial Leukocyte Adhesion Molecule 1: An Inducible Receptor for Neutrophils Related to Complement Regulatory Proteins and Lectins," *Science*, vol. 243, pp. 1160–1165 (Mar. 3, 1989).
Bevilacqua, M.P., et al., "Identification of an Inducible Endothelial–Leukocyte Adhesion Molecule," *Proc. Natl. Acad. Sci. USA*, vol. 84, pp. 9238–9242 (Dec. 1987).
Bevilacqua, M.P., et al., "Inducible Endothelial Functions in Inflammation and Coagulation," *Seminars in Thrombosis and Hemostasis*, vol. 13, No. 4, pp. 425–433 (1987).
Bonfanti, R., et al., "PADGEM (GMP140) is a Component of Weibel–Palade Bodies of Human Endothelial Cells," *Blood*, vol. 73, No. 5, pp. 1109–1112 (Apr., 1989).
Bowen, B.R., et al., "Characterization of a Human Homologue of the Murine Peripheral Lymph Node Homing Receptor," *J. Cell Bio.*, vol. 109, pp. 421–427 (Jul. 1989).
Brandley, B.K., et al., "Carbohydrate Ligands of the LEC Cell Adhesion Molecules," *Cell*, vol. 63, pp. 861–863 (Nov. 30, 1990).
Corral, L., et al., "Requirement of Sialic Acid on Neutrophils in a GMP–140 (PADGEM) Mediated Adhesive Interaction with Activated Platelets," *Biochem. Biophys. Res. Comm.*, vol. 172, No. 3, pp. 1349–1356 (Nov. 15, 1990).
Gamble, J.R., et al., "Prevention of Activated Neutrophil Adhesion to Endothelium by Soluble Adhesion Protein GMP140," *Science*, vol. 249, pp. 414–417 (Jul. 27, 1990).
Geng, J.G., et al., "Rapid Neutrophil Adhesion to Activated Endothelium Mediated by GMP–140," *Nature*, vol. 343, No. 6260, pp. 757–760 (Feb. 22, 1990).
Goelz, S.E., et al., "ELFT: A Gene That Directs the Expression of an ELAM–1 Ligand," *Cell*, vol. 63, pp. 1349–1356 (Dec. 21, 1990).
Hamburger, Steven A., et al., "GMP–140 Mediates Adhesion of Stimulated Platelets to Neutrophils," *Blood*, vol. 75, No. 3, pp. 550–554 (Feb. 1, 1990).

(List continued on next page.)

*Primary Examiner*—Sally P. Teng
*Attorney, Agent, or Firm*—Arnall Golden & Gregory, LLP

[57] ABSTRACT

Peptides derived from three regions of the lectin domain of GMP-140 (P-selectin) and the related selectins, ELAM-1 (E-selectin) and the lymphocyte homing receptor (L-selectin), have been found to inhibit neutrophil adhesion to GMP-140. These and additional peptides have been synthesized, having as their core region portions of the 74–76 amino acid sequence of GMP-140, with residue 1 defined as the N-terminus of the mature protein after the cleavage of the signal peptide. Examples demonstrate the inhibition of the binding of neutrophils to GMP-140 of peptides in concentrations ranging from 30 to 1500 μmol. It has been found that alterations within the core sequence, as well as N-terminal and C-terminal flanking regions, do not result in loss of biological activity. The peptides are useful as diagnostics and, in combination with a suitable pharmaceutical carrier, for clinical applications in the modulation or inhibition of coagulation processes or inflammatory processes.

12 Claims, 1 Drawing Sheet

OTHER PUBLICATIONS

Hattori, R., et al., "Complement C5b–9 Stimulates von Willebrand Factor Secretion from Human Endothelium," Arteriosclerosis, 8, 649–650, 1988, Meeting Abstract.

Hattori, R., et al., "Stimulated Secretion of Endothelial von Willebrand Factor is Accompanied by Rapid Redistribution to the Cell Surface of the Intracellular Granule Membrane Protein GMP–14," J. Biol. Chem., vol. 264, No. 14, pp. 7768–7771 (May 15, 1989).

Hattori, R., et al., "Complement Proteins C5b–9 Induce Secretion of High Molecular Weight Multimers of Endothelial von Willebrand Factor and Translocation of Granule Membrane Protein GMP–140 to the Cell Surface," J. Biol. Chem., vol. 264, No. 15, pp. 9053–9060 (1989).

Hourcade, D., et al., "The Regulators of Complement Activation (RCA) Gene Cluster," Advances in Immunology, vol. 45, pp. 381–415 (1989).

Issenberg, William M., et al., "Cell–Cell Contact Zones of Thrombin–Induced Platelet Aggregates Lack GPIIB–IIIA and Its Ligands but Contain GMP–140," Blood, 70:351a, Supplement, Abstract 1261 (Nov. 1987).

Issekutz, A., et al., "Role of Neutrophils in the Deposition of Platelets During Acute Inflammation," Laboratory Invest., vol. 49, No. 6, pp. 716–724 (1983).

Johnston, G.I., et al., "Cloning of GMP–140: Chromosomal Localization, Molecular Heterogeneity and Identification of cDNAs Predicting Both Membrane Bound and Soluble Proteins," Blood 72:327, Supplement Abstract 1218, (Nov. 1988).

Johnston, G.I., et al., "Cloning of GMP–140, a Granule Membrane Protein of Platelets and Endothelium: Sequence Similarity to Proteins Involved in Cell Adhesion and Inflammation," Cell, vol. 56, pp. 1033–1044 (Mar. 24, 1989).

Johnston, G.I., et al., "Platelet–Leukocyte Interaction: Selective Binding of Thrombin–Stimulated Platelets to Human Monocytes, Polymorphonuclear Leukocytes, and Related Cell Lines," Blood 70(5), Suppl. 1:352a Abstract No. 1264 (1987).

Johnston, G.I., et al., "Structural and Biosynthetic Studies of the Granule Membrane Protein, GMP–140, from Human Platelets and Endothelial Cells," J. Biol. Chem. vol. 264, No. 3, pp. 1816–1823 (1989).

Johnston, G.I., et al., "Structure and Biosynthesis of the Platelet $\alpha$–Granule Membrane Protein, GMP–140," Blood, 70(5), Suppl. 1:352a, Abstract 1264, (1987).

Johnston, G.I., et al., "Structure of the Human Gene Encoding Granule Membrane Protein–140, a Member of the Selectin Family of Adhesion Receptors for Leukocytes," J. Biol. Chem. vol. 265, No. 34, pp. 21381–21385 (Dec. 5, 1990).

Larsen, et al., "PADGEM Protein: A Receptor that Mediates the Interaction of Activated Platelets with Neutrophils and Monocytes," Cell, vol. 59, pp. 305–312 (Oct. 20, 1989).

Larsen, E., et al., "PADGEM–Dependent Adhesion of Platelets to Monocytes and Neutrophils Is Mediated by a Lineage–Specific Carbohydrate, LNF III (CD15)," Cell, vol. 63, pp. 467–474 (Nov. 2, 1990).

Lasky, L.A., et al., "Cloning of a Lymphocyte Homing Receptor Reveals a Lectin Domain," Cell, vol. 56, pp. 1045–1055 (Mar. 24, 1989).

Lawrence, M.B., et al., "Leukocytes Roll on a Selectin at Physiologic Flow Rates: Distinction from and Prerequisite for Adhesion through Integrins," Cell, vol. 65, pp. 1–20 (May 31, 1991).

Ley, Klaus, et al., "Lectin–Like Cell Adhesion Molecule 1 Mediates Leukocyte Rolling in Mesenteric Venules In Vivo," Blood, vol. 77, No. 12, pp. 2553–2555 (Jun. 15, 1991).

Lorant, Diane E., et al., "Coexpression of GMP–140 and PAF by Endothelium Stimulated by Histamine or Thrombin: A Juxtacrine System for Adhesion and Activation of Neutrophils," The Journal of Cell Biology, vol. 115, No. 1, pp. 223–234 (Oct. 1991).

Lowe, J.B., et al., " ELAM–1—Dependent Cell Adhesion to Vascular Endothelium Determined by a Transfected Human Fucosyltransferase cDNA," Cell, vol. 63, pp. 475–484 (Nov. 2, 1990).

McEver, R., et al., "A Monoclonal Antibody to a Membrane Glycoprotein Binds Only to Activated Platelets," J. Biol. Chem.., vol. 259, No. 15, pp. 9799–9804 (Aug. 10, 1984).

McEver, R., et al., "GMP–140, a Platelet $\alpha$–Granule Membrane Protein, Is Also Synthesized by Vascular Endothelial Cells and Is Localized in Weibel–Palade Bodies," J. Clin. Invest., vol. 84, pp. 92–99 (Jul. 1989).

McEver, R., et al., "GMP–140: A Receptor for Neutrophils and Monocytes on Activated Platelets and Endothelium," Journal of Cellular Biochemistry vol. 45, pp. 1–6 (1990).

McEver, R., et al., "The Platelet $\alpha$–Granule Membrane Protein GMP–140 is Also Synthesized by Human Vascular Endothelial Cells and is Present in Blood VEssels of Diverse Tissues," Blood 70(5) Suppl. 1:355a, Abstract No. 1274 (1987).

McEver, R., et al., "Properties of GMP–140, an Inducible Granule Membrane Protein of Platelets and Endothelium," Blood Cells, vol. 16, pp. 73–83 (1990).

McEver, R., "Selectins: Novel Receptors that Mediate Leukocyte Adhesion During Inflammation," Thrombosis and Haemostasis Review Article, F.K. Schattauer Verlagsgesellschaft mbH (Stuttgart) 65 (3) 223–228 (1991).

Mileski, W.J., et al., "Inhibition of CD17–Dependent Neutrophil Adherence Reduces Organ Injury after Hemorrhagic Shock in Primates," Surgery, vol. 108, No. 2, pp. 206–212 (Aug. 1990).

Mileski, W.J., et al., "Transient Inhibition of Neutrophil Adherence with the Anti–CD18 Monoclonal Antibody 60.3 Does Not Increase Mortality Rates in Abdominal Sepsis," Surgery, vol. 109, No. 4, pp. 497–501 (Apr. 1991).

Moore, K.L., et al., "GMP–140 Binds to a Glycoprotein Receptor on Human Neutrophils: Evidence for a Lectin–like Interaction," J. Cell Biol., vol. 112, pp. 491–499 (1991).

Müller–Eberhard, H., "Molecular Organization and Function of the Complement System," Ann. Rev. Biochem. vol. 57, pp. 321–347 (1988).

Ord, D.C., et al., "Structure of the Gene Encoding the Human Leukocyte Adhesion Molecule–1)TQ1, Leu–8) of Lymphocytes and Neutrophils," The Journal of Biological Chemistry, vol. 265, No. 14, pp. 7760–7767 (1990).

Patel, K.D., et al., "Oxygen Radicals Induce Human Endothelial Cells to Express GMP–140 and Bind Neutrophils," J. Cell. Biol., vol. 112, No. 4, pp. 749–759 (Feb. 1991).

Phillips, M.L., et al., "ELAM–1 Mediates Cell Adhesion by Recognition of a Carbohydrate Ligand, Sialyl–Le$^x$," Science, vol. 250, pp. 1130–1131 (Nov. 23, 1990).

Picker, Louis J., et al., "ELAM–1 is an Adhesion Molecule for Skin–homing T Cells," Nature, vol. 349, pp. 796–799 (Feb. 1991).

Rosen, S.D., "The LEC–CAMs' An Emerging Family of Cell Adhesion Receptors Based upon Carbohydrate Recognition," *Am. J. Respir. Cell Mol. Biol.,* vol. 3, pp. 397–402 (1990).

Shimizu, Yoii, et al., "Activation–independent Binding of Human Memory T Cells to Adhesion Molecule ELAM–1," *Nature,* vol. 349, pp. 799–802, (Feb. 1991).

Siegelman, M.H., et al., "Human Homologue of Mouse Lymph Node Homing Receptor: Evolutionary Conservation at Tandem Cell Interaction Domains," *Proc. Natl. Aca. Sci.,* vol. 86, pp. 5562–5566 (Jul. 1989).

Siegelman, M.H., et al., "Mouse Lymph Node Homing Receptor cDNA Clone Encodes a Glycoprotein Revealing Tandem Interaction Domains," *Science,* vol. 243, pp. 1165–1172 (Mar. 3, 1989).

Skinner, Michael P., et al., "Characterization of Human Platelet GMP–140 as a Heparin–Binding Protein," *Biochem. Biophys. Res. Comm.,* vol. 164, pp. 1373–1379 (1989).

Skinner, Michael P., et al., "GMP–140 Binding to Neutrophils is Inhibited by Sulfated Glycans," Journal of Biological Chemistry, vol. 266, No. 9, pp. 5371–5374 (Mar. 25, 1991).

Springer, T.A., et al., "Sticky Sugars for Selectins," *Nature,* vol. 349, pp. 196–197 (Jan. 17, 1991).

Stenberg, P., et al., "A Platelet Alpha–Granule Membrane Protein (GMP–140) is Expressed on the Plasma Membrane after Activation," *J. Cell Biol.,* vol. 101, pp. 880–886 (1985).

Tedder, T., et al., "Isolation and Chromosomal Localization of cDNAs Encoding a Novel Human Lymphocyte Cell Surface Molecule, LAM–1," *J. Exp. Med.* vol. 170, pp. 123–133 (Jul. 1989).

Tiemeyer, M., et al., "Carbohydrate Ligands for Endothelial–Leukocyte Adhesion Molecule 1," *Proc. Natl. Acad. Sci.,* vol. 88, pp. 1138–1142 (Feb. 1991).

Matuo et al., In Vitro Cell Dev. Biol., 25, 581–584, 1989.

Vedder, N.B., et al., "A Monoclonal Antibody to the Adherence–Promoting Leukocyte Glycoprotein, CD18, Reduces Organ Injury and Improves Survival from Hemorrhagic Shock and Resuscitation in Rabbits," *J. Clin. Invest.,* vol. 81, pp. 939–944 (Mar. 1988).

von Andrian, Ulrich H., et al., "Two Step Model of Leukocyte–Endothelial Cell Interaction in Inflammation: Distinct Roles for LECAM–1 and the Leukocyte $\beta 2$ Integrins In Vivo," *Proc. Natl. Acad. Sci.,* vol. 88, No. 17 pp. 7538–7542 (Sep. 1, 1991).

Walz, G., et al., "Recognition by ELAM–1 of the Sialyl–Le$^x$ Determinant on Myeloid and Tumor Cells," Science, vol. 250, pp. 1132–1135 (Nov. 23, 1990).

Watson, Mark L., et al., "Genomic Organization of the Selectin Family of Leukocyte Adhesion Molecules on Human and Mouse Chromosome 1," *J. Exp. Med.,* vol. 172, pp. 263–271 (Jul. 1990).

Watson, Susan R., et al., "Neutrophil Influx into an Inflammatory Site Inhibited by a Soluble Homing Receptor–IgG Chimaera," *Nature,* vol. 349, pp. 164–167 (Jan. 10, 1991).

Yednock, Ted A., et al., "Lymphocyte Homing," *Advances in Immunology,* vol. 44, pp. 313–378 (1989).

Zimmerman, Guy A., et al., "Thrombin Stimulates Neutrophil Adherence by an Endothelial Cell–Dependent Mechanism: Characterization of the Response and Relationship to Platelet–Activating Factor Synthesis," *Annals New York Academy of Sciences,* vol. 485, pp. 349–368 (1986).

Simpson, P.J., et al., "Reduction of Experimental Canine Myocardial Reperfusion Injury by a Monoclonal Antibody (Anti–Mo Anti–CD11b) That Inhibits Leukocyte Adhesion," *J. Clin. Invest.,* vol. 81, pp. 624–629 (Feb. 1988).

Jungi, et al., "Platelet–Leukocyte Interaction: Selective Binding of Thrombin–Stimulated Platelets to Human Monocytes, Polymorphonuclear Leukocytes, and Related Cell Lines," *Blood* 67:629–636 (1986).

Wang et al., Proc. Natl. Acad. Sci., 83, 6159–63, 1986.

Good et al., Proc. Natl. Acad. Sci, 85, 1199–203, 1988.

```
                        SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
           (A) LENGTH: 13 amino acids
           (B) TYPE:  amino acid
           (C) STRANDEDNESS:  single
           (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
           (A) ORGANISM:  Homo sapiens (xi) SEQUENCE DESCRIPTION:  SEQ ID NO:1:

Lys Lys Ala Leu Thr Asn Glu Ala Glu Asn Trp Ala Asp
1               5                  10

(2) INFORMATION FOR SEQ ID NO: 2:

(i) SEQUENCE CHARACTERISTICS:
           (A) LENGTH: 14 amino acids
           (B) TYPE:  amino acid
           (C) STRANDEDNESS:  single
           (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
           (A) ORGANISM:  Homo sapiens (xi) SEQUENCE DESCRIPTION:  SEQ ID NO:2:

Lys Lys Ala Leu Thr Asn Glu Ala Glu Asn Trp Ala Asp Asn
1               5                  10
```

```
(2) INFORMATION FOR SEQ ID NO: 3:

(i) SEQUENCE CHARACTERISTICS:
        (A) LENGTH: 14 amino acids
        (B) TYPE:  amino acid
        (C) STRANDEDNESS: single
        (D) TOPOLOGY:  linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Homo sapiens (xi) SEQUENCE DESCRIPTION: SEQ ID NO:3:

Cys Lys Ala Leu Thr Asn Glu Ala Glu Asn Trp Ala Asp Asn
1               5                  10

(2) INFORMATION FOR SEQ ID NO: 4:

(i) SEQUENCE CHARACTERISTICS:
        (A) LENGTH: 24 amino acids
        (B) TYPE:  amino acid
        (C) STRANDEDNESS: single
        (D) TOPOLOGY:  linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Homo sapiens (xi) SEQUENCE DESCRIPTION: SEQ ID NO:4:

Lys Lys Ala Leu Thr Asn Glu Ala Glu Asn Trp Ala Asp Asn Glu Pro
1               5                  10                  15

Asn Asn Lys Arg Asn Asn Glu Asp
            20

(2) INFORMATION FOR SEQ ID NO: 5:

(i) SEQUENCE CHARACTERISTICS:
        (A) LENGTH: 11 amino acids
        (B) TYPE:  amino acid
        (C) STRANDEDNESS: single
        (D) TOPOLOGY:  linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Homo sapiens (xi) SEQUENCE DESCRIPTION: SEQ ID NO:5:

Ala Leu Thr Asn Glu Ala Glu Asn Trp Ala Asp
1               5                  10

(2) INFORMATION FOR SEQ ID NO: 6:
```

```
        (i) SEQUENCE CHARACTERISTICS:
            (A) LENGTH: 11 amino acids
            (B) TYPE:  amino acid
            (C) STRANDEDNESS:  single
            (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
            (A) ORGANISM:  Homo sapiens (xi) SEQUENCE DESCRIPTION:  SEQ ID NO:6:

Ala Leu Thr Asn Glu Ala Gln Asn Trp Ala Asp
1               5                  10

(2) INFORMATION FOR SEQ ID NO: 7:

(i) SEQUENCE CHARACTERISTICS:
            (A) LENGTH: 9 amino acids
            (B) TYPE:  amino acid
            (C) STRANDEDNESS:  single
            (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
            (A) ORGANISM:  Homo sapiens (xi) SEQUENCE DESCRIPTION:  SEQ ID NO:7:

Thr Asn Glu Ala Glu Asn Trp Ala Asp
1               5

(2) INFORMATION FOR SEQ ID NO: 8:

(i) SEQUENCE CHARACTERISTICS:
            (A) LENGTH: 10 amino acids
            (B) TYPE:  amino acid
            (C) STRANDEDNESS:  single
            (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
            (A) ORGANISM:  Homo sapiens (xi) SEQUENCE DESCRIPTION:  SEQ ID NO:8:

Thr Asn Glu Ala Glu Asn Trp Ala Asp Asn
1               5                  10

(2) INFORMATION FOR SEQ ID NO: 9:

(i) SEQUENCE CHARACTERISTICS:
            (A) LENGTH: 10 amino acids
            (B) TYPE:  amino acid
```

```
            (C) STRANDEDNESS:  single
            (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
          (A) ORGANISM:  Homo sapiens (xi) SEQUENCE DESCRIPTION:  SEQ ID NO:9:

Thr Asn Ile Ala Gly Ile Trp Ala Trp Asn
1               5                  10

(2) INFORMATION FOR SEQ ID NO: 10:

(i) SEQUENCE CHARACTERISTICS:
          (A) LENGTH: 11 amino acids
          (B) TYPE:  amino acid
          (C) STRANDEDNESS:  single
          (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
          (A) ORGANISM:  Homo sapiens (xi) SEQUENCE DESCRIPTION:  SEQ ID NO:10:

Thr Asn Glu Ala Glu Asn Trp Ala Asp Asn Glu
1               5                  10

(2) INFORMATION FOR SEQ ID NO: 11:

(i) SEQUENCE CHARACTERISTICS:
          (A) LENGTH: 12 amino acids
          (B) TYPE:  amino acid
          (C) STRANDEDNESS:  single
          (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
          (A) ORGANISM:  Homo sapiens (xi) SEQUENCE DESCRIPTION:  SEQ ID NO:11:

Thr Asn Glu Ala Glu Asn Trp Ala Asp Asn Glu Pro
1               5                  10

(2) INFORMATION FOR SEQ ID NO: 12:

(i) SEQUENCE CHARACTERISTICS:
          (A) LENGTH: 17 amino acids
          (B) TYPE:  amino acid
          (C) STRANDEDNESS:  single
          (D) TOPOLOGY:  linear (ii) MOLECULE TYPE:  peptide
```

(iii) HYPOTHETICAL:  NO (iv) ANTI-SENSE:  NO (v) FRAGMENT TYPE:  N-terminal (vi) ORIGINAL SOURCE:
              (A) ORGANISM:  Homo sapiens (xi) SEQUENCE DESCRIPTION:  SEQ ID NO:12:

Ala Glu Asn Trp Ala Asp Asn Glu Pro Asn Asn Lys Arg Asn Asn Glu
1               5                  10                  15

Asp (2) INFORMATION FOR SEQ ID NO: 13:

(i) SEQUENCE CHARACTERISTICS:
              (A) LENGTH: 14 amino acids
              (B) TYPE:  amino acid
              (C) STRANDEDNESS:  single
              (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
              (A) ORGANISM:  Homo sapiens (xi) SEQUENCE DESCRIPTION:  SEQ ID NO:13:

Thr Asn Glu Ala Glu Asn Trp Ala Asp Asn Glu Pro Asn Asn
1               5                  10

(2) INFORMATION FOR SEQ ID NO: 14:

(i) SEQUENCE CHARACTERISTICS:
              (A) LENGTH: 9 amino acids
              (B) TYPE:  amino acid
              (C) STRANDEDNESS:  single
              (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
              (A) ORGANISM:  Homo sapiens (xi) SEQUENCE DESCRIPTION:  SEQ ID NO:14:

Asn Glu Ala Glu Asn Trp Ala Asp Asn
1               5

(2) INFORMATION FOR SEQ ID NO:15:

(i) SEQUENCE CHARACTERISTICS:
              (A) LENGTH: 10 amino acids
              (B) TYPE:  amino acid
              (C) STRANDEDNESS:  single
              (D) TOPOLOGY:  linear (ii) MOLECULE TYPE:  peptide (iii) HYPOTHETICAL:  NO

```
        (iv) ANTI-SENSE:  NO (v) FRAGMENT TYPE:  N-terminal (vi) ORIGINAL SOURCE:
             (A) ORGANISM:  Homo sapiens (xi) SEQUENCE DESCRIPTION:  SEQ ID NO:15:

Arg Lys Glu Ala Glu Ile Trp Thr Asp Val
1               5                  10

(2) INFORMATION FOR SEQ ID NO:16:

(i) SEQUENCE CHARACTERISTICS:
             (A) LENGTH: 11 amino acids
             (B) TYPE:  amino acid
             (C) STRANDEDNESS:  single
             (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
             (A) ORGANISM:  Homo sapiens (xi) SEQUENCE DESCRIPTION:  SEQ ID NO:16:

Ala Glu Asn Trp Ala Asp Asn Glu Pro Asn Asn
1               5                  10

(2) INFORMATION FOR SEQ ID NO:17:

(i) SEQUENCE CHARACTERISTICS:
             (A) LENGTH: 10 amino acids
             (B) TYPE:  amino acid
             (C) STRANDEDNESS:  single
             (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
             (A) ORGANISM:  Homo sapiens (xi) SEQUENCE DESCRIPTION:  SEQ ID NO:17:

Lys Trp Lys Trp Asn Arg Thr Asn Val Thr
1               5                  10

(2) INFORMATION FOR SEQ ID NO:18:

(i) SEQUENCE CHARACTERISTICS:
             (A) LENGTH: 7 amino acids
             (B) TYPE:  amino acid
             (C) STRANDEDNESS:  single
             (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal
```

(vi) ORIGINAL SOURCE:
              (A) ORGANISM: Homo sapiens (xi) SEQUENCE DESCRIPTION: SEQ ID NO:18:

Cys Leu Ala Ser Gly Ile Trp
1               5

(2) INFORMATION FOR SEQ ID NO:19:

(i) SEQUENCE CHARACTERISTICS:
              (A) LENGTH: 24 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
              (A) ORGANISM: Homo sapiens (xi) SEQUENCE DESCRIPTION: SEQ ID NO:19:

Gly Leu Leu Leu Val Gly Ala Ser Val Leu Gln Cys Leu Ala Thr Gly
1               5                   10                  15

Asn Trp Asn Ser Val Pro Pro Glu
              20

(2) INFORMATION FOR SEQ ID NO:20:

(i) SEQUENCE CHARACTERISTICS:
              (A) LENGTH: 21 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
              (A) ORGANISM: Homo sapiens (xi) SEQUENCE DESCRIPTION: SEQ ID NO:20:

Leu Glu Met Asn Tyr Tyr Gly Lys Gln Glu Asn Trp Tyr Ser Glu Lys
1               5                   10                  15

Lys Asn Ser Arg Cys
              20

(2) INFORMATION FOR SEQ ID NO:21:

(i) SEQUENCE CHARACTERISTICS:
              (A) LENGTH: 21 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO

```
        (v) FRAGMENT TYPE:  N-terminal (vi) ORIGINAL SOURCE:
            (A) ORGANISM:  Homo sapiens (xi) SEQUENCE DESCRIPTION:  SEQ ID NO:21:

Arg Ile Leu Ala Val Glu Arg Tyr Leu Lys Asp Gln Gln Leu Leu Gly
1               5                   10                  15

Ile Trp Gly Cys Ser
            20

(2) INFORMATION FOR SEQ ID NO:22:

(i) SEQUENCE CHARACTERISTICS:
            (A) LENGTH: 13 amino acids
            (B) TYPE:  amino acid
            (C) STRANDEDNESS:  single
            (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
            (A) ORGANISM:  Homo sapiens (ix) FEATURE:
            (A) NAME/KEY:  alternate amino acids
            (B) LOCATION:  1
            (D) OTHER INFORMATION:  amino acid 1 can be Lys, Gln, or Asn (ix) FEATURE:
            (A) NAME/KEY:  alternate amino acids
            (B) LOCATION:  3
            (D) OTHER INFORMATION:  amino acid 3 can be Ala, Pro, or Ser (ix) FEATURE:
            (A) NAME/KEY:  alternate amino acids
            (B) LOCATION:  6
            (D) OTHER INFORMATION:  amino acid 6 can be Asn or Glu (ix) FEATURE:
            (A) NAME/KEY:  alternate amino acids
            (B) LOCATION:  12
            (D) OTHER INFORMATION:  amino acid 12 can be Ala or Gly (ix) FEATURE:
            (A) NAME/KEY:  alternate amino acids
            (B) LOCATION:  13
            (D) OTHER INFORMATION:  amino acid 13 can be Asp or Pro (xi) SEQUENCE DESCRIPTION:  SEQ ID NO:22:

Xaa Lys Xaa Leu Thr Xaa Glu Ala Glu Asn Trp Xaa Xaa
1               5                   10

(2) INFORMATION FOR SEQ ID NO:23:

(i) SEQUENCE CHARACTERISTICS:
            (A) LENGTH: 11 amino acids
            (B) TYPE:  amino acid
            (C) STRANDEDNESS:  single
            (D) TOPOLOGY:  linear (ii) MOLECULE TYPE:  peptide (iii) HYPOTHETICAL:  NO (iv) ANTI-SENSE:  NO
```

```
        (v) FRAGMENT TYPE:  N-terminal (vi) ORIGINAL SOURCE:
            (A) ORGANISM:  Homo sapiens (ix) FEATURE:
            (A) NAME/KEY:  alternate amino acids
            (B) LOCATION:  5
            (D) OTHER INFORMATION:  amino acid 5 can be Ala or Gly (ix) FEATURE:
            (A) NAME/KEY:  alternate amino acids
            (B) LOCATION:  6
            (D) OTHER INFORMATION:  amino acid 6 can be Asp or Pro (ix) FEATURE:
            (A) NAME/KEY:  alternate amino acids
            (B) LOCATION:  7
            (D) OTHER INFORMATION:  amino acid 7 can be Asn or Gly (xi) SEQUENCE DESCRIPTION:  SEQ ID NO:23:

Ala Glu Asn Trp Xaa Xaa Xaa Glu Pro Asn Asn
1               5                   10

(2) INFORMATION FOR SEQ ID NO:24:

(i) SEQUENCE CHARACTERISTICS:
            (A) LENGTH: 13 amino acids
            (B) TYPE:  amino acid
            (C) STRANDEDNESS:  single
            (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
            (A) ORGANISM:  Homo sapiens (ix) FEATURE:
            (A) NAME/KEY:  alternate amino acids
            (B) LOCATION:  5
            (D) OTHER INFORMATION:  amino acid 5 can be Ala or Gly (ix) FEATURE:
            (A) NAME/KEY:  alternate amino acids
            (B) LOCATION:  6
            (D) OTHER INFORMATION:  amino acid 6 can be Asp or Pro (ix) FEATURE:
            (A) NAME/KEY:  alternate amino acids
            (B) LOCATION:  7
            (D) OTHER INFORMATION:  amino acid 7 can be Asn or Gly (ix) FEATURE:
            (A) NAME/KEY:  alternate amino acids
            (B) LOCATION:  12
            (D) OTHER INFORMATION:  amino acid 12 can be Lys or Arg (ix) FEATURE:
            (A) NAME/KEY:  alternate amino acids
            (B) LOCATION:  13
            (D) OTHER INFORMATION:  amino acid 13 can be Arg, Gln, or Lys (xi) SEQUENCE DESCRIPTION:  SEQ ID NO:24:

Ala Glu Asn Trp Xaa Xaa Xaa Glu Pro Asn Asn Xaa Xaa
1               5                   10

(2) INFORMATION FOR SEQ ID NO:25:

(i) SEQUENCE CHARACTERISTICS:
```

(A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Homo sapiens (ix) FEATURE:
            (A) NAME/KEY: alternate amino acids
            (B) LOCATION: 5
            (D) OTHER INFORMATION: amino acid 5 can be Ala or Gly (ix) FEATURE:
            (A) NAME/KEY: alternate amino acids
            (B) LOCATION: 6
            (D) OTHER INFORMATION: amino acid 6 can be Asp or Pro (ix) FEATURE:
            (A) NAME/KEY: alternate amino acids
            (B) LOCATION: 7
            (D) OTHER INFORMATION: amino acid 7 can be Asn or Gly (ix) FEATURE:
            (A) NAME/KEY: alternate amino acids
            (B) LOCATION: 12
            (D) OTHER INFORMATION: amino acid 12 can be Lys or Arg (ix) FEATURE:
            (A) NAME/KEY: alternate amino acids
            (B) LOCATION: 13
            (D) OTHER INFORMATION: amino acid 13 can be Arg, Gln, or Lys (ix) FEATURE:
            (A) NAME/KEY: alternate amino acids
            (B) LOCATION: 14
            (D) OTHER INFORMATION: amino acid 14 can be Asn or Lys (ix) FEATURE:
            (A) NAME/KEY: alternate amino acids
            (B) LOCATION: 15
            (D) OTHER INFORMATION: amino acid 15 can be Asn, Asp, or Lys (xi) SEQUENCE DESCRIPTION: SEQ ID NO:25:

Ala Glu Asn Trp Xaa Xaa Xaa Glu Pro Asn Asn Xaa Xaa Xaa Xaa Glu
1               5                   10                  15

Asp (2) INFORMATION FOR SEQ ID NO:26:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Homo sapiens (ix) FEATURE:

```
        (A) NAME/KEY:  alternate amino acids
        (B) LOCATION:  3
        (D) OTHER INFORMATION:  amino acid 3 can be Asn, Val, or Ile (ix) FEATURE:
        (A) NAME/KEY:  alternate amino acids
        (B) LOCATION:  4
        (D) OTHER INFORMATION:  amino acid 4 can be Asn or Gly (ix) FEATURE:
        (A) NAME/KEY:  alternate amino acids
        (B) LOCATION:  5
        (D) OTHER INFORMATION:  amino acid 5 can be Lys, Asn or Gly (ix) FEATURE:
        (A) NAME/KEY:  alternate amino acids
        (B) LOCATION:  6
        (D) OTHER INFORMATION:  amino acid 6 can be Thr, Val, or Ile (ix) FEATURE:
        (A) NAME/KEY:  alternate amino acids
        (B) LOCATION:  8
        (D) OTHER INFORMATION:  amino acid 8 can be Thr or Val (ix) FEATURE:
        (A) NAME/KEY:  alternate amino acids
        (B) LOCATION:  13
        (D) OTHER INFORMATION:  amino acid 13 can be Lys, Gln, or Asn (ix) FEATURE:
        (A) NAME/KEY:  alternate amino acids
        (B) LOCATION:  15
        (D) OTHER INFORMATION:  amino acid 15 can be Ala, Pro, or Ser (ix) FEATURE:
        (A) NAME/KEY:  alternate amino acids
        (B) LOCATION:  18
        (D) OTHER INFORMATION:  amino acid 18 can be Asn or Glu (xi) SEQUENCE DESCRIPTION:  SEQ ID NO:26:

Arg Lys Xaa Xaa Xaa Xaa Trp Xaa Trp Val Gly Thr Xaa Lys Xaa Leu
1               5                   10                  15

Thr Xaa Glu (2) INFORMATION FOR SEQ ID NO:27:

(i) SEQUENCE CHARACTERISTICS:
        (A) LENGTH: 10 amino acids
        (B) TYPE:  amino acid
        (C) STRANDEDNESS:  single
        (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
        (A) ORGANISM:  Homo sapiens (ix) FEATURE:
        (A) NAME/KEY:  alternate amino acids
        (B) LOCATION:  3
        (D) OTHER INFORMATION:  amino acid 3 can be Asn, Val, or Ile (ix) FEATURE:
        (A) NAME/KEY:  alternate amino acids
        (B) LOCATION:  4
        (D) OTHER INFORMATION:  amino acid 4 can be Asn or Gly (ix) FEATURE:
        (A) NAME/KEY:  alternate amino acids
        (B) LOCATION:  5
```

```
            (D) OTHER INFORMATION:  amino acid 5 can be Lys, Asn or Gly (ix) FEATURE:
            (A) NAME/KEY:  alternate amino acids
            (B) LOCATION:  6
            (D) OTHER INFORMATION:  amino acid 6 can be Thr, Val, or Ile (ix) FEATURE:
            (A) NAME/KEY:  alternate amino acids
            (B) LOCATION:  8
            (D) OTHER INFORMATION:  amino acid 8 can be Thr or Val (xi) SEQUENCE DESCRIPTION:  SEQ ID NO:27:

Arg Lys Xaa Xaa Xaa Xaa Trp Xaa Trp Val
1               5                   10

(2) INFORMATION FOR SEQ ID NO:28:

(i) SEQUENCE CHARACTERISTICS:
            (A) LENGTH:  7 amino acids
            (B) TYPE:  amino acid
            (C) STRANDEDNESS:  single
            (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
            (A) ORGANISM:  Homo sapiens (xi) SEQUENCE DESCRIPTION:  SEQ ID NO:28:

Gly Gly Ile Trp Thr Trp Val
1               5

(2) INFORMATION FOR SEQ ID NO:29:

(i) SEQUENCE CHARACTERISTICS:
            (A) LENGTH:  6 amino acids
            (B) TYPE:  amino acid
            (C) STRANDEDNESS:  single
            (D) TOPOLOGY:  linear (ii) MOLECULE TYPE:  peptide (iii) HYPOTHETICAL:  NO (iv) ANTI-SENSE:  NO (v) FRAGMENT TYPE:  N-terminal (vi) ORIGINAL SOURCE:
            (A) ORGANISM:  Homo sapiens (xi) SEQUENCE DESCRIPTION:  SEQ ID NO:29:

Gly Ile Trp Thr Trp Val
1               5
```

PEPTIDE INHIBITORS OF INFLAMMATION MEDIATED BY SELECTINS

This is a continuation of application Ser. No. 07/809,942 filed on Dec. 18, 1991, now abandoned.

BACKGROUND OF THE INVENTION

This invention is generally in the field of methods for the treatment and prevention of inflammatory responses using peptides derived from selectins.

The adherence of platelets and leukocytes to vascular surfaces is a critical component of the inflammatory response, and is part of a complex series of reactions involving the simultaneous and interrelated activation of the complement, coagulation, and immune systems.

Endothelium exposed to "rapid" activators such as thrombin and histamine becomes adhesive for neutrophils within two to ten minutes, while endothelium exposed to cytokines such as tumor necrosis factor and interleukin-1 becomes adhesive after one to six hours. The rapid endothelial-dependent leukocyte adhesion has been associated with expression of the lipid mediator platelet activating factor (PAF) on the cell surface, and the appearance of other endothelial and leukocyte surface receptors.

The selectins are three structurally related membrane glycoproteins that participate in leukocyte adhesion to vascular endothelium and platelets, as reviewed by McEver *Thromb. Haemostas.* 66:80–87 (1991). P-selectin (CD62), previously known as GMP-140 or PADGEM protein, is a receptor for neutrophils and monocytes that is rapidly translocated from secretory granule membranes to the plasma membranes of activated platelets, as reported by Larsen, et al., in *Cell* 59, 305–312 (October 1989) and Hamburger and McEver, *Blood* 75:550–554 (1990), and endothelial cells, as reported by Geng, et al., *Nature* 343:757–760 (1990) and Lorant, et al., *J. Cell Biol.* 115:223–234 (1991). E-selectin (ELAM-1) is a cytokine-inducible endothelial cell receptor for neutrophils, as reported by Bevilacqua *Proc. Natl. Acad. Sci. USA* 84:9238–9242 (1987), monocytes, as reported by Hession, et al., *Proc. Natl. Acad. Sci. USA* 87:1673–1677 (1990), and memory T cells, as reported by Picker, et al. *Nature* 349:796–799 (1991) and Shimizu, et al. *Nature* 349:799–802 (1991). L-selectin (LAM-1, LECAM-1, Leu-8/Mel 14/TQ1 antigen, lymphocyte homing receptor), a protein expressed on myeloid cells and most lymphocytes, participates in neutrophil extravasation into inflammatory sites and homing of lymphocytes to peripheral lymph nodes, as reported by Laskey, et al., *Cell* 56:1045–1055 (1989), Siegelman, et al., *Science* 243:1165–1172 (1989); Kishimoto, et al., *Science* 245:1238–1241 (1989); Watson, et al., *Nature* 349–164–167 (1991).

The slower cytokine-inducible endothelial adhesion for leukocytes is mediated, at least in part, by E-selectin (ELAM-1), that is synthesized by endothelial cells after exposure to cytokines and then transported to the cell surface, where it binds neutrophils. The isolation, characterization and cloning of ELAM-1 is reviewed by Bevilacqua, et al., in *Science* 243, 1160–1165 (1989). L-selectin was characterized and cloned as reported by Lasky, et al., *Cell* 56, 1045–1055 (1989) (mouse) and Tedder, et al., *J. Exp. Med.* 170, 123–133 (1989). P-selectin (GMP-140) was first purified from human platelets by McEver and Martin, *J. Biol. Chem.* 259:9799–9804 (1984). The protein is present in alpha granules of resting platelets but is rapidly redistributed to the plasma membrane following platelet activation, as reported by Stenberg, et al., (1985). The presence of P-selectin in endothelial cells and its biosynthesis by these cells was reported by McEver, et al., *Blood* 70(5) Suppl. 1:355a, Abstract No. 1274 (1987).

Proteins involved in the hemostatic and inflammatory pathways are of interest for diagnostic purposes and treatment of human disorders. However, there are many problems using proteins therapeutically. Proteins are usually expensive to produce in quantities sufficient for administration to a patient. Moreover, there can be a reaction against the protein after it has been administered more than once to the patient. It is therefore desirable to develop peptides having the same, or better, activity as the protein, which are inexpensive to synthesize, reproducible and relatively innocuous.

The function of GMP-140 (P-selectin) for use in inhibiting an inflammatory response was described by McEver in U.S. Ser. No. 07/320,408, filed Mar. 8, 1989, now U.S. Pat. No. 5,378,464. Peptides derived from GMP-140 are described in the continuation-in-part application U.S. Ser. No. 07/554,199, now abandoned, entitled "Functionally Active Selectin-Derived Peptides" filed Jul. 17, 1990 by Rodger P. McEver that are useful in diagnostics and in modulating the hemostatic and inflammatory responses in a patient wherein a therapeutically effective amount of a peptide capable of blocking leukocyte recognition of GMP-140 (P-selectin) is administered to the patient. U.S. Ser. No. 07/554,199 filed Jul. 17, 1990, now abandoned, also discloses that peptide sequences within the lectin domain of GMP-140, having homology with the lectin domains of other proteins, especially ELAM-1 (E-selectin) and the homing receptor (L-selectin), selectively inhibit neutrophil adhesion to purified GMP-140, and can therefore be used in diagnostic assays of patients and diseases characterized by altered binding by these molecules, in screening assays for compounds altering this binding, and in clinical applications to inhibit or modulate interactions of leukocytes with platelets or endothelial cells involving coagulation and/or inflammatory processes.

U.S. Ser. No. 07/757,131, now abandoned, entitled "Peptide Inhibitors of Inflammation Mediated by Selectins" filed Sep. 10, 1991 by George A. Heavner, Rodger P. McEver, and Jian-Guo Geng, and U.S. Ser. No. 07/699,693 filed May 14, 1991, now abandoned, disclose synthetic peptides derived from the core regions of GMP-140, residues 56–60 and residues 23–30, respectively. These peptides are useful in inhibiting binding of the selectins. It is preferable to develop peptides which can be prepared synthetically, having activity at least equal to, or greater than, the peptides derived from the protein itself.

It is therefore an object of the present invention to provide peptides interacting with cells recognized by selectins, including P-selectin, E-selectin and L-selectin.

It is another object of the present invention to provide methods for using these peptides to inhibit leukocyte adhesion to endothelium or to platelets.

It is a further object of the present invention to provide methods for using these peptides to modulate the immune response and the hemostatic pathway.

It is yet another object of the present invention to provide peptides for use in diagnostic assays relating to P-selectin, E-selectin and L-selectin.

SUMMARY OF THE INVENTION

Peptides derived from three regions of the lectin domain of P-selectin (GMP-140) and the related selectins, E-selectin (ELAM-1) and L-selectin (the lymphocyte homing receptor), have been found to inhibit selectin-mediated binding, for example, neutrophil adhesion to GMP-140 (P-selectin). These and additional peptides have been synthesized having the following formula:

$$R^1\text{-}X\text{-}A\text{-}B\text{-}C\text{-}Y\text{-}R^2 \qquad (I)$$

or a pharmaceutically acceptable acid- or based-addition thereof wherein:

A is D- or L-glutamic acid or glycine;

B is D- or L-asparagine or D- or L-isoleucine;

C is D- or L-tryptophan;

X and Y are linear chains of from 0 to 16 amino acids;

$R^1$ is H (signifying a free N-terminal primary amino group), formyl, lower alkyl, aryl, lower alkanoyl, aroyl, alkyloxycarbonyl or aryloxycarbonyl and $R^2$ is OH (signifying a free C-terminal carboxyl group), lower alkyl or aryl esters, or $NR^3R^4$ where $R^3$ and $R^4$ each selected independently from H, lower alkyl or aryl.

Peptides of Formula I have as their core region portions of the 74–76 amino acid sequence of GMP-140, with residue 1 defined as the N-terminus of the mature protein after the cleavage of the signal peptide. Examples of peptides of Formula I demonstrate the inhibition of the binding of neutrophils to P-selectin in concentrations ranging from 30 to 1500 μm. It has been found that alterations within the core sequence, as well as N-terminal and C-terminal flanking regions, do not result in loss of biological activity.

The peptides are useful as diagnostics and, in combination with a suitable pharmaceutical carrier, for clinical applications in the modulation or inhibition of coagulation processes or inflammatory processes.

DETAILED DESCRIPTION OF THE INVENTION

Figure 1:
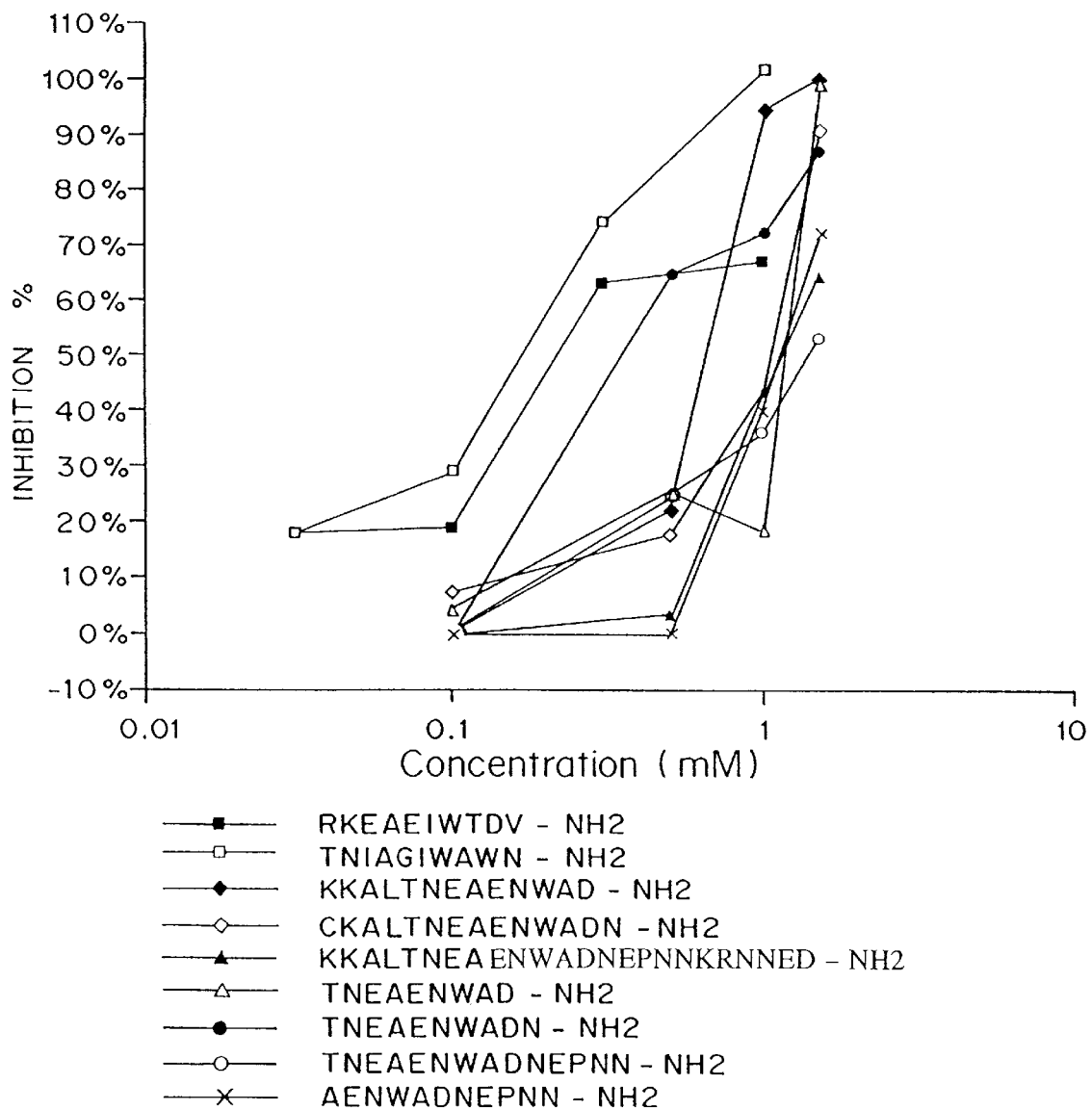
FIG. 1 shows the activity of several peptides of Formula I in inhibiting the binding of neutrophils to GMP-140, percent inhibition versus concentration of peptide (mM). RKEAEIWTDV-NH$_2$(SEQ ID NO:15) (dark squares); TNIAGIWAWN-NH$_2$(SEQ ID NO:9) (open squares); KKALTNEAENWAD-NH$_2$(SEQ ID NO:1) (dark diamonds); CKALTNEAENWADN-NH$_2$(SEQ ID NO:3) (open diamonds); KKALTNEAENWADNEPNNKRNNED-NH$_2$(SEQ ID NO:4) (DARK TRIANGLES); TNEAENWAD-NH$_2$(SEQ ID NO:7) (open triangles); TNEAENWADN-NH$_2$(SEQ ID NO:8) (dark circles); TNEAENWADNEPNN-NH$_2$(SEQ ID NO:13) (open circles); and AENWADNEPNN-NH$_2$(SEQ ID NO:16) (X).

Peptides, defined as consisting of between three and one hundred amino acids, having P-selectin-like activity, therapeutic compositions containing these peptides, methods for the preparation of these peptides, and methods of use thereof are disclosed.

In their broadest scope, the peptides have the following formula:

$$R^1\text{-}X\text{-}A\text{-}B\text{-}C\text{-}Y\text{-}R^2 \qquad (I)$$

or a pharmaceutically acceptable salt thereof, wherein:

A is D- or L-glutamic acid or glycine;

B is D- or L-asparagine or D- or L-isoleucine;

C is D- or L-tryptophan;

X and Y are linear chains of from 0 to 16 amino acids;

$R^1$ is H (signifying a free N-terminal primary amino group), formyl, lower alkyl, aryl, lower alkanoy, aroyl, alkyloxycarbonyl or aryloxycarbonyl and $R^2$ is OH (signifying a free C-terminal carboxyl group), lower alkyl or aryl esters, or $NR^3R^4$ where $R^3$ and $R^4$ are each selected independently from H, lower alkyl or aryl. Preferred peptides are those wherein C is L-tryptophan, particularly where $R^1$ is H and $R^2$ is $NR^3R^4$.

Most preferred peptides are:

```
Lys-Lys-Ala-Leu-Thr-Asn-Glu-Ala-Glu-Asn-Trp-Ala-Asp-NH₂           (Sequence ID NO. 1)

Lys-Lys-Ala-Leu-Thr-Asn-Glu-Ala-Glu-Asn-Trp-Ala-Asp-Asn-NH₂       (Sequence ID NO. 2)

Cys-Lys-Ala-Leu-Thr-Asn-Glu-Ala-Glu-Asn-Trp-Ala-Asp-Asn-NH₂       (Sequence ID NO. 3)

Lys-Lys-Ala-Leu-Thr-Asn-Glu-Ala-Glu-Asn-Trp-Ala-Asp-Asn-          (Sequence ID NO. 4)
Glu-Pro-Asn-Asn-Lys-Arg-Asn-Asn-Glu-Asp-NH₂

Ala-Leu-Thr-Asn-Glu-Ala-Glu-Asn-Trp-Ala-Asp                       (Sequence ID NO. 5)

Ala-Leu-Thr-Asn-Glu-Ala-Gln-Asn-Trp-Ala-Asp-NH₂                   (Sequence ID NO. 6)

Thr-Asn-Glu-Ala-Glu-Asn-Trp-Ala-Asp-NH₂                           (Sequence ID NO. 7)

Thr-Asn-Glu-Ala-Glu-Asn-Trp-Ala-Asp-Asn-NH₂                       (Sequence ID NO. 8)

Thr-Asn-Ile-Ala-Gly-Ile-Trp-Ala-Trp-Asn-NH₂                       (Sequence ID NO. 9)

Acetyl-Thr-Asn-Glu-Ala-Glu-Asn-Trp-Ala-Asp-Asn-NH₂                (Sequence ID NO. 8)

Thr-Asn-Glu-Ala-Glu-Asn-Trp-Ala-Asp-Asn-Glu-NH₂                   (Sequence ID NO. 10)

Thr-Asn-Glu-Ala-Glu-Asn-Trp-Ala-Asp-Asn-Glu-Pro-NH₂               (Sequence ID NO. 11)

Thr-Asn-Glu-Ala-Glu-Asn-Trp-Ala-Asp-Asn-Glu-Pro-Asn-Asn-NH₂       (Sequence ID NO. 13)

Asn-Glu-Ala-Glu-Asn-Trp-Ala-Asp-Asn-NH₂                           (Sequence ID NO. 14)
```

```
Ala-Glu-Asn-Trp-Ala-Asp-Asn-Glu-Pro-Asn-Asn-NH2              (Sequence ID NO. 16)

Ala-Glu-Asn-Trp-Ala-Asp-Asn-Glu-Pro-Asn-Asn-Lys-Arg-Asn-     (Sequence ID NO. 12)
Asn-Glu-Asp Ala-Glu-Asn-Trp-Ala-Asp-Asn-Glu-Pro-Asn-Asn-Lys-Arg-Asn-     (Sequence ID NO. 12)
Asn-Glu-Asp-NH2

Arg-Lys-Glu-Ala-Glu-Ile-Trp-Thr-Asp-Val-NH2.                 (Sequence ID NO. 15)
```

As used herein, the term "lower alkyl" includes branched, straight-chain, and cyclic saturated hydrocarbons having from one to six carbon atoms, such as methyl, ethyl, propyl, isopropyl, butyl, isobutyl, t-butyl, pentyl, isopentyl, neopentyl, and hexyl. The term "lower alkanoyl" means RC(O), wherein R is a lower alkyl group. The term aroyl means where ArC(O), wherein Ar is an aryl group, an aromatic or heteroaromatic structure having between one and three rings, which may or may not be ring fused structures, and are optimally substituted with halogens, carbons, or other heteroatoms such as nitrogen (N), sulfur (S), phosphorus (P), and boron (B).

The peptides of formula I can be used in the form of the free peptide or a pharmaceutically acceptable salt. Amine salts can be prepared by mixing the peptide with an acid according to known methods. Suitable acids include inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid, and sulfanilic acid.

Carboxylic acid groups in the peptide can be converted to a salt by mixing the peptide with a base according to known methods. Suitable bases include inorganic bases such as sodium hydroxide, ammonium hydroxide, and potassium hydroxide, and organic bases such as mono-, di-, and tri-alkyl and aryl amines (e.g., triethylamine, disopropylamine, methylamine, and dimethylamine and optionally substituted mono-, di, and tri-ethanolamines).

As referred to herein, the amino acid components of the peptides and certain materials used in their preparation are identified by abbreviations for convenience. These abbreviations are as follows:

|  | Abbreviations | |
|---|---|---|
| Amino Acid | | |
| L-alanine | Ala | A |
| D-alanine | D-Ala | a |
| L-allosoleucine | AIle | |
| P-alloisoleucine | D-AIle | |
| L-arginine | Arg | R |
| D-arginine | D-Arg | r |
| D-asparagine | D-Asn | N |
| L-asparagine | L-Asn | n |
| L-aspartic acid | Asp | D |
| D-aspartic acid | D-Asp | d |
| L-cysteine | Cys | C |
| D-cysteine | D-Cys | c |
| L-glutamic acid | Glu | E |
| D-glutamic acid | D-Glu | e |
| L-glutamine | Gln | Q |

| -continued | | |
|---|---|---|
|  | Abbreviations | |
| D-glutamine | D-Gln | q |
| glycine | Gly | G |
| L-histidine | His | H |
| D-histidine | D-His | h |
| L-isolelucine | Ile | I |
| D-isoleucine | D-Ile | i |
| L-leucine | Leu | L |
| D-leucine | D-Leu | l |
| L-lysine | Lys | K |
| D-lysine | D-Lys | k |
| L-phenylalanine | Phe | F |
| D-phenylalanine | D-Phe | f |
| L-proline | Pro | P |
| D-proline | D-Pro | p |
| L-pyroglutamic acid | pGlu | |
| D-pyroglutamic acid | D-pGlu | |
| L-serine | L-Ser | S |
| D-serine | D-Ser | s |
| L-threonine | L-Thr | T |
| D-threonine | D-Thr | t |
| L-tyrosine | L-Tyr | Y |
| D-tyrosine | D-Tyr | y |
| L-tryptophan | Trp | W |
| D-tryptophan | D-Trp | w |
| L-valine | Val | V |
| D-valine | D-Val | v |
| Reagents | | |
| Trifluoroacetic acid | TFA | |
| Methylene chloride | $CH_2Cl_2$ | |
| N,N-Diisopropylethylamine | DIEA | |
| N-Methylpyrrolidone | NMP | |
| 1-Hydroxybenzotriazole | HOBT | |
| Dimethylsulfoxide | DMSO | |
| Acetic anhydride | $Ac_2O$ | |

Methods of Preparation of Peptides

The peptides can generally be prepared following known techniques, as described for example in the cited publications, the teachings of which are specifically incorporated herein. In a preferred method, the peptides are prepared following the solid-phase synthetic technique initially described by Merrifield in *J.Amer.Chem.Soc.*, 85, 2149–2154 (1963). Other techniques may be found, for example, in M. Bodanszky, et al., *Peptide Synthesis*, second edition, (John Wiley & Sons, 1976), as well as in other reference works known to those skilled in the art.

Appropriate protective groups usable in such syntheses and their abbreviations will be found in the above text, as well as in J. F. W. McOmie, *Protective Groups in Organic Chemistry*, (Plenum Press, New York, 1973). The common protective groups used herein are t-butyloxycarbonyl (Boc), fluorenylmethoxycarbonyl (FMOC), benzyl (Bzl), tosyl (Tos), o-bromo-phenylmethoxycarbonyl (BrCBZ or BrZ), phenylmethoxycarbonyl (CBZ or Z), 2-chlorophenylmethoxycarbonyl, (2-Cl-CBZ or Cl-Z), 4-methoxy- 2,3,6-trimethylbenzenesulfonyl (Mtr), formyl (CHO), and tertiary butyl (t-Bu).

General synthetic procedures for the synthesis of peptides of Formula I by solid phase methodology are as follows:

|  | REPETITIONS | TIME |
|---|---|---|
| A. General Synthetic Procedures for Solid Phase Peptide Synthesis Using $N^\alpha$-Boc Protection. | | |
| 1. 25% TFA in $CH_2Cl_2$ | 1 | 3 min |
| 2. 50% TFA in $CH_2Cl_2$ | 1 | 16 min |
| 3. $CH_2Cl_2$ | 5 | 3 min |
| 4. 5% DIEA in NMP | 2 | 4 min |
| 5. NMP | 6 | 5 min |
| 6. Coupling step | 1 | 57 min |
| a. Preformed BOC-Amino Acid-HOBT active ester in NMP | | 36 min |
| b. DMSO | | 16 min |
| c. DIEA | | 5 min |
| 7. 10% $Ac_2O$, 5% DIEA in NMP | 1 | 9 min |
| 8. $CH_2Cl_2$ | 5 | 3 min |
| B. General Synthetic Procedure For Solid Phase Peptide Synthesis Using $N^\alpha$-FMOC Protection | | |
| 1. 20% piperidine in NMP | 1 | 3 min |
| 2. 20% piperidine in NMP | 1 | 15 min |
| 3. NMP | 6 | 9 min |
| 4. Coupling Preformed FMOC-Amino Acid-HOBT active ester in NMP | 1 | 71 min |
| 5. NMP | 6 | 7 min |

N-terminal acetylation on the deprotected $N^\alpha$-amino group of peptides synthesized using either Boc or FMOC strategies is accomplished with 10% $Ac_2O$ and 5% DIEA in NMP, followed by washing of the peptide resin with NMP and/or $CH_2Cl_2$.

The peptides can also be prepared using standard genetic engineering techniques known to those skilled in the art. For example, the peptide can be produced by inserting nucleic acid encoding the peptide into an expression vector, expressing the DNA, and translating the RNA into the peptide in the presence of the required amino acids. The peptide is then purified using chromatographic or electrophoretic techniques, or by means of a carrier protein which can be fused to, and subsequently cleaved from, the peptide by inserting into the expression vector in phase with the peptide encoding sequence a nucleic acid sequence encoding the carrier protein. The fusion protein-peptide may be isolated using chromatographic, electrophoretic or immunological techniques (such as binding to a resin via an antibody to the carrier protein). The peptide can be cleaved using chemical methodology or enzymatically, as by, for example, hydrolases.

Methods of Preparation of Pharmaceutical Compositions

To prepare the pharmaceutical compositions containing these peptides, a peptide of Formula I or a base or acid addition salt thereof is combined as the active ingredient with a pharmaceutical carrier according to conventional pharmaceutical compounding techniques. This carrier may take a wide variety of forms depending on the form of preparation desired for administration, e.g., sublingual, rectal, nasal, oral, or parenteral. In preparing the compositions in oral dosage form, any of the usual pharmaceutical media may be employed, for example, water, oils, alcohols, flavoring agents, preservatives, and coloring agents, to make an oral liquid preparation (e.g., suspension, elixir, or solution) or with carriers such as starches, sugars, diluents, granulating agents, lubricants, binders, and disintegrating agents, to make an oral solid preparation (e.g., powder, capsule, or tablet).

Controlled release forms or enhancers to increase bioavailability may also be used. Because of their ease in administration, tablets and capsules represent the most advantageous oral dosage unit form, in which case solid pharmaceutical carriers are employed. If desired, tablets may be sugar coated or enteric coated by standard techniques.

For parenteral products, the carrier will usually be sterile water, although other ingredients to aid solubility or as preservatives may be included. Injectable suspensions may also be prepared, in which case appropriate liquid carriers and suspending agents can be employed.

The peptides can also be administered locally at a wound or inflammatory site by topical application of a solution or cream.

Alternatively, the peptide may be administered in liposomes. or microspheres (or microparticles) or other embedded or encapsulated delivery systems. Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A good review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the peptide can be incorporated and the microspheres, or composite of microspheres, implanted for slow release over a period of time, ranging from days to months. See, for example, U.S. Pat. Nos. 4,906,474, 4,925,673, and 3,625,214.

Methods for Demonstrating Binding

Peptides that are biologically active are those which inhibit binding of neutrophils, monocytes, subsets of lymphocytes or other cells to selectins such as GMP-140, or which inhibit leukocyte adhesion to endothelium that is mediated by ELAM-1 and/or the homing receptor.

Peptides can be screened for their ability to inhibit adhesion to cells, for example, neutrophil adhesion to purified GMP-140 immobilized on plastic wells, using the assay described by Geng, et al., *Nature* 343, 757–760 (1990).

Human neutrophils are isolated from heparinized whole blood by density gradient centrifugation on Mono-Poly resolving media, Flow Laboratories. Neutrophil suspensions are greater than 98% pure and greater than 95% viable by trypan blue exclusion. For adhesion assays, neutrophils are suspended at a concentration of $2 \times 10^6$ cells/ml in Hanks' balanced salt solution containing 1.26 mM $Ca^{2+}$ and 0.81 mM $Mg^{2+}$ (HBSS, Gibco) with 5 mg/ml human serum albumin (HBSS/HSA). Adhesion assays are conducted in triplicate in 96-well microtiter plates, Corning, incubated at 4° C. overnight with 50 microliters of various protein solutions.

GMP-140 is isolated from human platelet lysates by immunoaffinity chromatography on antibody S12-Sepharose™ and ion-exchange chromatography on a Mono-Q™ column (FLPC, Pharmacia Fine Chemicals), as follows.

Outdated human platelet packs (100 units) obtained from a blood bank and stored at 4° C. are pooled, adjusted to 5 mM EDTA at pH 7.5, centrifuged at 4,000 rpm for 30 min in 1 liter bottles, then washed three times with 1 liter of 0.1 M NaCl, 20 mM Tris pH 7.5 (TBS), 5 mM EDTA, 5 mM benzamidine.

The pellets are then resuspended in a minimum amount of wash buffer and made 1 mM in DIFP, then frozen in 50 ml screwtop tubes at −80° C. The frozen platelets are thawed and resuspended in 50 ml TBS, 5 mM benzamidine, 5 mM EDTA pH 7.5, 100 M leupeptin. The suspension is frozen and thawed two times in a dry ice-acetone bath using a 600 ml lyophilizing flask, then homogenized in a glass/teflon mortar and pestle and made 1 mM in DIFP. The NaCl concentration is adjusted to 0.5 M with a stock solution of 4 M NaCl. After stirring the suspension at 4° C., it is centrifuged in polycarbonate tubes at 33,000 rpm for 60 min at 4° C. The supernatant (0.5 M NaCl wash) is removed and saved. Care is taken not to remove the top part of the pellet with the supernatant. The pellets are then homogenized in extraction buffer (TBS, 5 mM benzamidine, 5 mM EDTA, pH 7.5, 100 $\mu$M leupeptin, 2% Triton X-100). After centrifugation at 19,500 rpm for 25 min at 4° C., the supernatant is removed. The extraction procedure is repeated with the pellet and the supernatant is combined with the first supernatant. The combined extracts, which contain the membrane form of GMP-140, are adjusted to 0.5 M NaCl.

The soluble fraction (0.5 M NaCl wash) and the membrane extract (also adjusted to 0.5 M NaCl) are absorbed with separate pools of the monoclonal antibody S12 (directed to human GMP-140) previously coupled to Affigel (Biorad) at 5 mg/ml for 2 h at 4° C. After letting the resins settle, the supernatants are removed. The S12 Affigel containing bound GMP-140 is then loaded into a column and washed overnight at 4° C. with 400 ml of 0.5 M NaCl, 20 mM Tris pH 7.5, 0.01% Lubrol PX.

Bound GMP-140 is eluted from the S12 Affigel with 100 ml of 80% ethylene glycol, 1 mM MES pH 6.0, 0.01% Lubrol PX. Peak fractions with absorbance at 280 nm are pooled. Eluates are dialyzed against TBS with 0.05% Lubrol, then applied to a Mono Q column (FPLC from Pharmacia). The concentrated protein is step eluted with 2 M NaCl, 20 mM Tris pH 7.5 (plus 0.05% Lubrol PX for the membrane fraction). Peak fractions are dialyzed into TBS pH 7.5 (plus 0.05% Lubrol PX for the membrane fraction).

GMP-140 is plated at 5 micrograms/ml and the control proteins: human serum albumin (Alb), platelet glycoprotein IIb/IIIa (IIb), von Willebrand factor (vWF), fibrinogen (FIB), thrombomodulin (TM), gelatin (GEL) or human serum (HS), are added at 50 micrograms/ml. All wells are blocked for 2 h at 22° C. with 300 microliters HBSS containing 10 mg/ml HSA, then washed three times with HBSS containing 0.1% Tween-20 and once with HBSS. Cells ($2\times10^5$ per well are added to the wells and incubated at 22° C. for 20 min. The wells are then filled with HBSS/HSA, sealed with acetate tape (Dynatech), and centrifuged inverted at 150 g for 5 min. After discarding nonadherent cells and supernates, the contents of each well are solubilized with 200 microliters 0.5% hexadecyltrimethylammonium bromide, Sigma, in 50 mM potassium phosphate, pH 6.0, and assayed for myeloperoxidase activity, Ley, et al., *Blood* 73, 1324–1330 (1989). The number of cells bound is derived from a standard curve of myeloperoxidase activity versus numbers of cells. Under all assay conditions, the cells release less than 5% of total myeloperoxidase and lactate dehydrogenase.

Clinical Applications

The subject peptides are generally active when administered parenterally in amounts above about 1 g peptide/kg of body weight. For treatment to prevent organ injury in cases involving reperfusion, the peptides may be administered parenterally from about 0.01 to about 10 mg peptide/kg body weight. Generally, the same range of dosage amounts may be used in treatment of the other diseases or conditions where inflammation is to be reduced. This dosage will be dependent, in part, on whether one or more peptides are administered. A synergistic effect may be seen with combinations of peptides from different, or overlapping, regions of the lectin domain, or in combination with peptides derived from the EGF domain of GMP-140.

Since the selectins have several functions related to leukocyte adherence, inflammation, and coagulation, clinically compounds which interfere with binding of GMP-140, ELAM-1 or LAM-1 can be used to modulate these responses.

For example, the peptides can be used to competitively inhibit leukocyte adherence by competitively binding to GMP-140 receptors on the surface of leukocytes. This kind of therapy would be particularly useful in acute situations where effective, but transient, inhibition of leukocyte-mediated inflammation is desirable. Chronic therapy by infusion of the peptides may also be feasible in some circumstances.

An inflammatory response may cause damage to the host if unchecked, because leukocytes release many toxic molecules that can damage normal tissues. These molecules include proteolytic enzymes and free radicals. Examples of pathological situations in which leukocytes can cause tissue damage include injury from ischemia and reperfusion, bacterial sepsis and disseminated intravascular coagulation, adult respiratory distress syndrome, tumor metastasis, rheumatoid arthritis and atherosclerosis.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., *Circulation* 67: 1016–1023, 1983). These adherent leukocytes can migrate through the endothelium and destroy ischemic myocardium just as it is being rescued by restoration of blood flow.

There are a number of other common clinical disorders in which ischemia and reperfusion results in organ injury mediated by adherence of leukocytes to vascular surfaces, including strokes; mesenteric and peripheral vascular disease; organ transplantation; and circulatory shock (in this case many organs might be damaged following restoration of blood flow).

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products.

Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (lymphokine-activated lymphocytes). LAK cells are known to adhere to vascular walls and release products that are presumably toxic to endothelium. Although the mechanism by which LAK cells adhere to endothelium is not known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. The association of platelets with metastasizing tumor cells has been well described, suggesting a role for platelets in the spread of some cancers.

Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia.

Another area of potential application is in the treatment of rheumatoid arthritis.

The criteria for assessing response to therapeutic modalities employing these peptides are dictated by the specific condition and will generally follow standard medical practices. For example, the criteria for the effective dosage to prevent extension of myocardial infarction would be determined by one skilled in the art by looking at marker enzymes of myocardial necrosis in the plasma, by monitoring the electrocardiogram, vital signs, and clinical response. For treatment of acute respiratory distress syndrome, one would examine improvements in arterial oxygen, resolution of pulmonary infiltrates, and clinical improvement as measured by lessened dyspnea and tachypnea. For treatment of patients in shock (low blood pressure), the effective dosage would be based on the clinical response and specific measurements of function of vital organs such as the liver and kidney following restoration of blood pressure. Neurologic function would be monitored in patients with stroke. Specific tests are used to monitor the functioning of transplanted organs; for example, serum creatinine, urine flow, and serum electrolytes in patients undergoing kidney transplantation.

Diagnostic Reagents

The peptides can also be used for the detection of human disorders in which the ligands for the selectins might be defective. Such disorders would most likely be seen in patients with increased susceptibility to infections in which leukocytes might not be able to bind to activated platelets or endothelium. Cells to be tested, usually leukocytes, are collected by standard medically approved techniques and screened. Detection systems include ELISA procedures, binding of radiolabeled antibody to immobilized activated cells, flow cytometry, or other methods known to those skilled in the arts. Inhibition of binding in the presence and absence of the lectin domain peptides can be used to detect defects or alterations in selectin binding. For selectins, such disorders would most likely be seen in patients with increased susceptibility to infections in which leukocytes would have defective binding to platelets and endothelium because of deficient leukocyte ligands for GMP-140. The peptide is labeled radioactively, with a fluorescent tag, enzymatically, or with electron dense material such as gold for electron microscopy. The cells to be examined, usually leukocytes, are incubated with the labeled peptides and binding assessed by methods described above with antibodies to GMP-140, or by other methods known to those skilled in the art. If ligands for GMP-140 are also found in the plasma, they can also be measured with standard ELISA or radioimmunoassay procedures, using labeled GMP-140-derived peptide instead of antibody as the detecting reagent.

The following examples are presented to illustrate the invention without intending to specifically limit the invention thereto. In the examples and throughout the specifications, parts are by weight unless otherwise indicated.

EXAMPLE 1

Preparation of Lysyl-lysyl-alanyl-leucyl-threonyl-asparaginyl-glutamyl-alanyl-glutamyl-asparaginyl-tryptophyl-alanyl-aspartic acid amide (Sequence ID No. 1).

The peptide was prepared on an ABI Model 431A Peptide Synthesizer using Version 1.12 of the standard BOC software. 4-methyl benzhydrylamine resin (0.62 g, 0.50 mmol) was used in the synthesis. The final weight of the resin was 1.46 g.

The peptide was cleaved from the resin (1.46 g) using 16 mL of HF, 1.5 mL anisole and 100 $\mu$L thiophenol for 60 min. at 0° C. The cleaved resin was washed with ether and peptide extracted with 25 mL of a solution of 50% TFA in methylene chloride. Evaporation of the solution and trituration of the residue gave 478 mg of crude peptide.

The tryptophan was deformylated using 100 mL of 0.1 M of aqueous piperidine for 1 hour at 0° C. The reaction mixture was evaporated and lyophilized.

The crude peptide (243 mg) was purified on a Vydac C-18 column (10, 2.2×25 cm) eluting with a 20–60% gradient of 50% acetonitrile in 0.1% TFA over 180 min. at a flow rate of 3 mL min. Fractions were collected, analyzed by HPLC and pure fractions pooled and lyophilized to give 35 mg. Amino acid analysis: Ala 3.00 (3), Asx 2.56 (3), Glx 2.03 (2), Leu 1.08 (1), Lys 2.10 (2), Thr 1.00 (1), Trp ND (1). FAB/MS: MH$^+$ 1489 (M.W. 1488.63).

EXAMPLE 2

Preparation of Cysteinyl-lysyl-alanyl-lucyl-threonyl-asparaginyl-glutamyl-alanyl-glutamyl-asparaginyl-tryptophyl-alanyl-aspartyl-asparagine amide (Sequence ID No. 3).

The peptide was prepared on an ABI Model 431A Peptide Synthesizer using Version 1.12 of the standard BOC software. 4-methyl benzhydrylamine resin (0.62 g, 0.50 mmol) was used in the synthesis. The peptide resin was washed with ethanol and dried. The final weight of the resin was 1.38 g.

The peptide was cleaved from the resin (1.30 g) using 13 mL of HF and anisole (1.3 mL), dithiothreitol (1.0 g) for 60 min at 0° C. The resin was washed with ether and the peptide extracted with a solution of 50% TFA in methylene chloride (3×12 mL) to give 760 mg of crude peptide. The formulated peptide was dissolved in DMF (20 mL) and 1% piperidine/water solution (50 mL) was added, stirred for one hour at 0° C. and lyophilized to yield 652 mg of crude peptide.

The crude peptide (650 mg) was purified on a Vydac C-18 column (15, 5×25 cm, 65 mg per injection) eluting with a 15 to 45% gradient of 80% acetonitrile in 0.1% TFA over 120 min at a flow rate of 15 mL per min. Fractions were collected, analyzed by HPLC and pure fractions pooled and lyophilized to give 17 mg of white powder. Amino acid analysis: Asx 3.58 (4), Thr 0.92 (1), Glx 1.99 (2), Ala 3.00 (3), Cys 1.04 (1), Leu 1.02 (1), Lys 0.98 (1), Trp 0.56 (1), FAB/MS: MH$^+$ 1578 (M.W. 1577.71).

EXAMPLE 3

Preparation of Lysyl-lysyl-alanyl-leucyl-threonyl-asparaginyl-glutamyl-alanyl-glutanyl-asparaginyl-tryptophyl-alanyl-aspartyl-asparaginyl-glutamyl-prolyl-asparaginyl-asparaginyl-lysyl-arginyl-asparaginyl-asparaginyl-glutasyl-aspartic acid amide (Sequence ID No. 4).

The peptide was prepared on an ABI Model 431A Peptide Synthesizer using Version 1.12 of the standard BOC software. 4-methyl benzhydrylamine resin (0.62 g, 0.50 mmol) was used in the synthesis. The final weight of the resin was 2.20 g.

The peptide was cleaved from the resin (2.06 g) using 20 mL of HF and 2 mL anisole for 60 min. at 0° C. The resin was washed with ether and extracted with a solution of 50% TFA in methylene chloride to give 0.78 g of crude peptide. The peptide was deformylated using 0.1M aqueous piperidine for 1 hr. at 0° C.

The crude peptide (500 mg) was purified on a Vydac C-18 column (10 , 2.2×25 cm) eluting with a gradient of 5–22% acetonitrile in 0.1% TFA over 160 min. at a flow rate of 3 mL per min. Fractions were collected, analyzed by HPLC and pure fractions pooled and lyophilized to give 36 mg. Amino acid analysis: Asx 7.90 (9); Thr 0.90 (1); Glx 4.08 (4); Ala 2.89 (3); Leu 0.99 (1); Lys 3.07 (3); Trp ND; Arg 0.96 (1). FAB/MS: MH$^+$ 2813 (M.W. 2813.96)

EXAMPLE 4

Preparation of Threonyl-asparaginyl-glutamyl-alanyl-glutamyl-asparaginyl-tryptophyl-alanyl-aspartic acid amide (Sequence ID No. 7).

The peptide was prepared on an ABI Model 431A Peptide Synthesizer using Version 1.12 of the standard BOC software. 4-methyl benzhydrylamine resin (0.62 g, 0.50 mmol) was used in the synthesis. The final weight of the resin was 1.18 g.

The peptide was cleaved from the resin (1.15 g) using 14 mL of HF, 1.2 mL anisole and 200 L thiophenol for 60 min. at 0° C. The resin was washed with ether and extracted with 50 mL of a solution of 50% TFA in methylene chloride. Evaporation of the solution and trituration of the residue with ether gave 0.43 g of crude peptide.

The tryptophan was deformylated using 100 mL of 0.1 M of aqueous piperidine for 1 hour at 0° C. The reaction mixture was evaporated and lyophilized.

The crude peptide (62 mg) was purified on a Vydac C-18 column (10, 2.2×25 cm) using an isocratic system of 18% acetonitrile in 0.1% TFA over 75 min. at a flow rate of 8 mL per min. Fractions were collected, analyzed by HPLC and pure fractions pooled and lyophilized to give 32 mg. Amino acid analysis: Ala 2.33 (2); Asx 2.38 (3), Glx 2.09 (2), Thr 0.88 (1), Trp ND (1). FAB/MS: MH$^+$ 1049 (M.W. 1048.04).

EXAMPLE 5

Preparation of Throonyl-asparaginyl-glutamyl-alanyl-glutamyl-asparaginyl-tryptophyl-alanyl-aspartyl asparagine amide (Sequence ID No. 8).

The peptide was prepared on an ABI Model 431A Peptide Synthesizer using Version 1.12 of the standard BOC software. 4-methyl benzhydrylamine resin (0.62 g, 0.50 mmol) was used in the synthesis. The final weight of the resin was 1.26 g.

The peptide was cleaved from the resin (1.20 g) using 12 mL of HF and 1.2 mL of anisole for 60 min at 0° C. The resin was washed with 1:1 methylene chloride/ether and the peptide extracted with 50% TFA in methylene chloride to give 620 mg of crude peptide.

The crude peptide (600 mg) was purified on a Vydac C-18 column (15, 5×25 cm) eluting with a 0–40% gradient of 80% acetonitrile in 0.1% TFA over 120 min at a flow rate of 25 mL per min. Fractions were collected, analyzed by HPLC and pure fractions pooled and lyophilized to give 84 mg of pure peptide. Amino acid analysis: Ala 2.00 (2), Asx 3.88 (4), Glx 2.06 (2), Thr 0.92 (1), Trp 0.62 (1). FAB/MS: MH$^+$ 1163 (M.W. 1162.15).

EXAMPLE 6

Preparation of Threonyl-asparaginyl-isoleucyl-alanyl-glycyl-isoleucyl-tryptophyl-alanyl-tryptophyl-asparagine amide (Sequence ID No. 9).

The peptide was prepared on an ABI Model 431A Peptide Synthesizer using Version 1.12 of the standard BOC software. 4-methyl benzhydrylamine resin (0.62 g, 0.50 mmol) was used in the synthesis. The peptide resin (1.25 g) was deformylated using a solution of 10% piperidine in N-methyl pyrrolidine (10 mL) for 2 hrs at 0° C. The final weight of the resin was 1.15 g.

The peptide was cleaved from the resin (1.15 g) using 12 mL of HF and 1.2 mL of anisole for 60 min at 0° C. The resin was washed with ether and the peptide extracted with a solution of 50% TFA in methylene chloride to give 358 mg of crude peptide.

The crude peptide (350 mg) was purified on a Vydac C-18 column (15, 5×25 cm) eluting with a 15–60% gradient of 80% acetonitrile in 0.1% TFA over 120 min at a flow rate of 15 mL per min. Fractions were collected, analyzed by HPLC and pure fractions pooled and lyophilized to give 93 mg of white solid. Amino acid analysis: Ala 2.02 (2), Asx 2.07 (2), Gly 1.03 (1), Ile 1.85 (2), Thr 0.93 (1), Trp 1.30 (2). FAB/MS: MH$^+$ 1144 (M.W. 1144.31).

EXAMPLE 7

Preparation of Threonyl-asparaginyl-glutamyl-alanyl-glutamyl-asparaginyl-tryptophyl-alanyl-aspartyl-asparaginyl-glutamic acid amide (Sequence ID No. 10).

The peptide was prepared on an ABI Model 431A Peptide Synthesizer using Version 1.12 of the standard BOC software. 4-methyl benzhydrylamine resin (0.62 g, 0.50 mmol) was used in the synthesis. The final weight of the resin was 1.32 g. The resin was treated with 1 M ethanolamine in DMF/5% water (2×30 min.) washed with DMF ethanol and dried to a constant weight.

The resin (1.17 g) was cleaved with 10 mL HF, 0.50 g p-creosol and 0.50 g p-thiocreosol for 1 hour at 0° C. The resin was washed with ether and the peptide extracted with a solution of 50% TFA in methylene chloride. After evaporation the residue was triturated with ether to give 0.75 g of a white solid.

300 mg of the crude material was purified on a Vydac C-18 column (10μ, 2.2×25 cm) using 0.1% TFA in 10% acetonitrile at a flow rate of 8 mL per min. Fractions were collected, analyzed by HPLC and pure fractions pooled, evaporated and lyophilized to give 37 mg of a white solid. Amino acid analysis: Ala 2.21 (2), Asx 3.26 (4), Glx 3.24 (3), Thr 0.95 (1), Trp ND (1). FAB/MS: MH$^+$ 1292 (M.W. 1291.26).

EXAMPLE 8
Preparation of Acetyl-threonyl-asparaginyl-glutamyl-alanyl-glutamyl-asparaginyl-tryptophyl-alanyl-aspartyl-asparagine amide (Sequence ID No. 8).

The peptide was prepared on an ABI Model 431A Peptide Synthesizer using Version 1.12 of the standard FMOC software. Bachem FMOC amide resin (0.59 g, 0.25 mmol) was used in the synthesis. The peptide was cleaved from the resin using 9 mL of TFA, 0.5 mL ethanedithiol and 0.5 mL p-cresol at 35° C. for 2 hr. Ether was added to precipitate the product which was isolated by filtration to give 0.22 g.

The crude peptide (0.22 g) was purified on a Vydac C-18 column (15, 5×25 cm) eluting with a 26–50% gradient of 50% acetonitrile in 0.1% TFA over 120 min. at a flow rate of 15 mL per min. Fractions were collected, analyzed by HPLC and pure fractions pooled and lyophilized to give 25 mg. Amino acid analysis: Asx 3.68 (4), Thr 0.97 (1), Glx 2.09 (2), Ala 2.07 (2), Trp ND (1). FAB/MS: MH$^+$ 1205 (M.W. 1204.18).

EXAMPLE 9
Preparation of Acetyl-threonyl-asparaginyl-glutamyl-alanyl-glutamyl-asparaginyl-tryptophyl-alanyl-aspartyl-asparaginyl-glutamyl-proline amide (Sequence ID No. 11).

The peptide was prepared on an ABI Model 431A Peptide Synthesizer using version 1.12 of the standard BOC software. 4-Methyl benzhydrylamine resin (0.62 g, 0.50 mmol) was used in the synthesis. The final weight of the peptide-resin was 1.43 g. The resin-peptide (1.29 g) was treated with 1.5 mL of anisole and 15 mL of HF for one hour at 0° to 4° C. The HF was removed by nitrogen stream followed by aspiration. The resultant solids were triturated with diethyl ether (2×30 mL), collected by filtration and washed with diethyl ether (3×30 mL). The resultant solids were extracted with cold 0.1 M piperidine (5×20 mL). The extracts were combined and stirred for one hour at 0° to 4° C. and then lyophilized. The yield of deformylated crude peptide was 774 mg. 524 mg of crude peptide was purified HPLC using a Vydac C-18 column (10μ, 2.2×25 cm) eluting with a gradient of 10% to 20% acetonitrile in 0.1% TFA over 120 minutes at a flow rate of 3 mL per min. Fractions were collected and the appropriate ones pooled to give 6 mg of off-white solid. Amino acid analysis: Ala 2.00 (2), Asx 3.10 (4), Glx 3.07 (3), Pro 0.98 (1), Thr 0.91 (1), Trp ND (1). FAB/MS: MH$^+$ 1389 (M.W. 1388.38).

EXAMPLE 10
Preparation of Threonyl-asparaginyl-glutaryl-alanyl-glutamyl-asparaginyl-tryptophyl-alanyl-aspartyl-asparaginyl-glutamyl-prolyl-asparaginyl-asparagine amide (Sequence ID No. 13).

The peptide was prepared on an ABI Model 431A Peptide Synthesizer using Version 1.12 of the standard BOC software. 4-methyl benzhydrylamine resin (0.80 g, 0.50 mmol) was used in the synthesis. The final weight of the resin was 1.30 g. The tryptophan was deformylated on the resin using 1 M ethanolamine in 5% aqueous DMF (2×30 min.). The peptide was cleaved from the resin (1.18 g) using 10 mL of HF and 1 mL of anisole for 60 min. at 0° C. The resin was washed with ether and extracted with 50% TFA in methylene chloride to give 0.44 g of crude peptide. The crude peptide was purified on a Vydac C-18 column (10μ, 2.2×25 cm) eluting with a 20–27% gradient of acetonitrile in 0.1% TFA over 45 min. at a flow rate of 8 mL per min. Fractions were collected, analyzed by HPLC and pure fractions pooled and lyophilized to give 33 mg. Amino acid analysis: Asx 5.88 (6), Thr 1.07 (1), Glx 2.61 (3), Pro 1.06 (1), Ala 2.18 (2), Trp ND (1). FABMS: MH$^+$ 1616 (M.W. 1616.59).

EXAMPLE 11
Preparation of Asparaginyl-glutamyl-alanyl-glutamyl-asparaginyl-tryptophyl-alanyl-aspartyl-asparagine amide (Sequence ID No. 14).

The peptide was prepared on an ABI Model 431A Peptide Synthesizer using Version 1.12 of the standard BOC software. 4-methyl benzhydrylamine resin (0.62 g, 0.50 mmol) was used in the synthesis. Peptidyl-resin was washed with ethanol and dried. The final weight of the resin was 1.14 g.

The peptide was cleaved from the resin (1.13 g) using 12 of HF and 1.2 mL of anisole for 60 min at 0° C. The resin was washed with ether and the peptide extracted with 1% piperidine/water (4×25 mL). Combined fractions were stirred for 1 hour at 0° C. then lyophilized to give 520 mg of crude peptide.

The crude peptide (500 mg) was purified on a Vydac C-18 column (15, 5×25 cm) eluting with a 10–30% gradient of 80% acetonitrile in 0.1% TFA over 120 min at a flow rate of 15 mL per min. Fractions were collected, analyzed by HPLC and pure fractions pooled and lyophilized to give 30 mg of white solid. Amino acid analysis: Ala 1.99 (2), Asx 3.92 (4), Glx 2.05 (2), Trp 0.64 (1). FAB/MS: MH$^+$ 1061 (MW 1061.04).

EXAMPLE 12
Preparation of Alanyl-glutamyl-asparaginyl-tryptophyl-alanyl-aspartyl-asparaginyl-glutanyl-prolyl-asparaginyl-asparagine amide (Sequence ID No. 16).

The peptide was prepared on an ABI Model 431A Peptide Synthesizer using Version 1.12 of the standard BOC software. 4-methyl benzhydrylamine resin (0.67 g, 0.54 mmol) was used in the synthesis. The final weight of the resin was 1.27 g.

The peptide was cleaved from the resin (1.18 g) using 10 mL of HF, 1 mL anisole for 60 min. at 0° C. The resin was washed with ether and extracted with a solution of 50% TFA in methylene chloride to give 0.55 g of crude peptide. The peptide was deformylated in 100 ml of 0.1 M aqueous piperidine for 60 min at 0° C.

The crude peptide (0.20 g) was purified on Vydac C-18 column (10, 2.2×25 cm) eluting with a gradient of 10–13.5% acetonitrile in 0.1% TFA over 45 min. at a flow rate of 8 mL per min. Fractions were collected, analyzed by HPLC and pure fractions pooled and lyophilized to give 40 mg. Amino acid analysis: Asx 4.36 (5); Glx 2.08 (2); Pro 1.03 (1); Ala 2.12 (2) Trp ND FAB/MS: MH$^+$ 1273 (M.W. 1272.26).

EXAMPLE 13
Preparation of Alanyl-glutamyl-asparaginyl-tryptophyl-alanyl-aspartyl-asparaginyl-glutamyl-prolyl-asparaginyl-lysyl-arginyl-asparaginyl-asparaginyl-glutamyl-asparagine amide (Sequence ID No. 12).

The peptide was prepared on an ABI Model 431A Peptide Synthesizer using version 1.12 of the standard BOC software. 4-Methyl benzhydrylamine resin (0.62 g, 0.05 mmol) was used in the synthesis. The final weight of the peptide-resin was 1.70 g. 1.6 g of the resin-peptide was treated with 1.6 mL of anisole and 16 mL of HF for one hour at 0° to 4° C. The HF was removed by nitrogen stream followed by aspiration. The resultant solids were triturated with diethyl ether (2×30 mL), collected by filtration and washed with diethyl ether (2×30 mL). The resultant solids were extracted with cold 0.1 M piperidine (5×20 mL). The extracts were stirred for one hour at 0° C. to 4° C. and then lyophilized. The yield of crude peptide was 1.24 g. The peptide was chromatographed on a Pharmacia Mono Q™ 10/16 column by elution with 0.02 M to 0.50 M ammonium bicarbonate over 600 mL at 6 mL/min. The appropriate fractions from 8 runs were pooled and lyophilized to give 172 mg of semi-pure peptide. The semi-pure peptide was further purified by reverse phase HPLC using a Vydac™ 22×250 mm C18 10 micron particle sized 300 Angstrom pore packed column, eluting with a gradient of 0% to 25% acetonitrile in 0.1% TFA over 45 minutes at a flow rate of 10 mL/min. Fractions were collected and the appropriate ones pooled to give 69 mg of white solid. Amino acid Analysis: Ala 2.07 (2), Arg 1.02 (1), Asx 7.46 (8), Glx 3.10 (3), Lys 0.98 (1), Pro 0.99 (1), Trp ND (1). FAB/MS MH+ 2030 (M.W. 2029.04).

EXAMPLE 14
Preparation of Arginyl-lysyl-glutamyl-alanyl-glutamyl-isoleucyl-tryptophyl-threonyl-aspartyl-valine amide (Sequence ID No. 15).

The peptide was prepared on an ABI Model 431A Peptide Synthesizer using Version 1.12 of the standard BOC software. 4-methyl benzhydrylamine resin (0.62 mg, 0.50 mmol) was used in the synthesis. The peptide resin was washed with ethanol and dried. The final weight of the resin was 1.52 g. The protected peptidyl-resin (1.5 g) was deformylated in 10% piperidine/N-methyl pyrrolidone solution (10 mL) at 0° C. for 2 hours. The peptide-resin was washed with N-methyl pyrrolidone, methylene chloride and methanol and dried to give 1.35 g.

The peptide was cleaved from the resin (1.3 g) using 13 mL of HF and 1.3 mL of anisole for 60 min at 0° C. The resin was washed with ether and ether/methylene chloride 1:1 and the peptide extracted with a solution of 50% TFA in methylene chloride (3×15 mL). The solvents were evaporated and the residue was treated with ether. The precipitate was removed by filtration, washed with ether and dried to give 674 mg of crude peptide.

The crude peptide (670 mg) was purified on a Vydac C-18 column (15, 5×25 cm) eluting with a 0–50% gradient of 80% acetonitrile in 0.1% TFA over 120 min at a flow rate of 15 mL per min. Fractions were collected, analyzed by HPLC and pure fractions pooled and lyophilized to give 287 mg of white solid. Amino acid analysis: Ala 0.99 (1), Arg 1.01 (1), Asx 1.02 (1), Glx 2.02 (2), Ile 0.95 (1), Lys 1.01 (1), Thr 0.89 (1), Trp 0.64 (1), Val 1.00 (1). FAB/MS: MH+ 1245.2 (M.W. 1245.41).

EXAMPLE 15
Inhibition of Neutrophil Binding to GMP140 Coated Wells.

Binding of various peptides to GMP-140 coated wells, as described above, were compared. The results are shown in FIG. 1 and summarized in Table 1.

Binding of the peptides at various concentrations, ranging from 0.03 to 1.5 mM, were compared. The peptides tested were: RKEAEIWTDV-NH$_2$; TNIAGIWAWN-NH$_2$; KKALTNEAENWAD-NH$_2$; CKALTNEAENWADN-NH$_2$; KKALTNEAENWADNEPNNKRNNED-NH$_2$; TNEAENWAD-NH$_2$; TNEAENWADN-NH$_2$; TNEAENWADNEPNN-NH$_2$; AENWADNEPNN-NH$_2$; TNEAENWADNE-NH$_2$; Ac-TNEAENWADN-NH$_2$; TNEAENWADNEP-NH$_2$; NEAENWADN-NH$_2$; AENWADNEPNNKRNNED-NH$_2$; and KWKWNRTNVT-NH$_2$ (Negative Control). The results demonstrate that the peptides, with the exception of the negative control, all inhibit neutrophil binding to immobilized GMP-140.

TABLE 1

PERCENT INHIBITION OF NEUTROPHIL BINDING

| STRUCTURE | | PEPTIDE CONCENTRATION (Mm) | | | | | | |
|---|---|---|---|---|---|---|---|---|
| | | 0.0 | 0.05 | 0.10 | 0.30 | 0.50 | 1.0 | 1.5 |
| RKEAEIWTDV-NH$_2$ | (SEQ ID NO:15) | | 18 | 19 | 63 | | 67 | |
| TNIAGIWAWN-NH$_2$ | (SEQ ID NO:9) | | 18 | 29 | 74 | | 102 | |
| KKALTNEAENWAD-NH$_2$ | (SEQ ID NO:1) | | | 0 | | 22 | 95 | 101 |
| CKALTNEAENWADN-NH$_2$ | (SEQ ID NO:3) | | | 7 | | 18 | 43 | 91 |
| KKALTNEAENWADNEPNNKRNNED-NH$_2$ | (SEQ ID NO:4) | | | 0 | | 3 | 43 | 64 |
| TNEAENWAD-NH$_2$ | (SEQ ID NO:7) | | | 4 | | 25 | 18 | 99 |
| TNEAENWADN-NH$_2$ | (SEQ ID NO:8) | | | 0 | | 64 | 72 | 87 |
| TNEAENWADNEPNN-NH$_2$ | (SEQ ID NO:13) | | | 0 | | 24 | 36 | 53 |
| AENWADNEPNN-NH$_2$ | (SEQ ID NO:16) | | | 0 | | 0 | 40 | 73 |
| TNEAENWADNE-NH$_2$ | (SEQ ID NO:10) | | | 1 | | 11 | 0 | 55 |
| Ac-TNEAENWADN-NH$_2$ | (SEQ ID NO:8) | | 9 | 0 | | 0 | 9 | 33 |
| TNEAENWADNEP-NH$_2$ | (SEQ ID NO:11) | | | | | 0 | 13 | 65 |
| NEAENWADN-NH$_2$ | (SEQ ID NO:14) | | | 1 | | 17 | 12 | 35 |

TABLE 1-continued

PERCENT INHIBITION OF NEUTROPHIL BINDING

| STRUCTURE | | PEPTIDE CONCENTRATION (Mm) | | | | | |
|---|---|---|---|---|---|---|---|
| | | 0.0 | 0.05 | 0.10 | 0.30 | 0.50 | 1.0 1.5 |
| AENWADNEPNNKRNNED-NH$_2$ | (SEQ ID NO:12) | 11 | 7 | | | 15 | 29 |
| KWKWNRTNVT-NH$_2$ | (SEQ ID NO:17) | | 0 | | | 0 | 0 0 |
| (Negative Control) | | | | | | | |

Modifications and variations of the present invention, synthetic peptides and methods for modulating binding reactions involving selectins, will be obvious to those skilled in the art from the foregoing detailed description. Such modifications and variations are intended to come within the scope of the appended claims.

We claim:

1. A peptide which inhibits binding of cells to a selectin, wherein the peptide is selected from the group having the formula:

$$R^1\text{-X-A-B-C-Y-}R^2$$

or a pharmaceutically acceptable acid- or base-addition salt thereof wherein:

$R^1$ is a moiety attached to the amine function ($NHR^1$) of the N-terminal amino acid and $R^2$ is the moiety attached to the carbonyl group of the C-terminal amino acid, A is D- or L-glutamic acid or glycine;

B is D- or L-asparagine or D- or L-isoleucine;

C is D- or L-tryptophan;

X and Y are linear chains of from 0 to 16 amino acids;

R¹ is H, formyl, lower alkyl, aryl, lower alkanoyl, aroyl, alkyloxycarbonyl or aryloxycarbonyl and R² is OH, O(lower alkyl), O(aryl), or NR³R⁴ where R³ and R⁴ are independently H, lower alkyl or aryl, with the proviso that if R¹ is H, R² is OH, and X, A, B, C, and Y comprise L-amino acids, then (1) X-A-B-C-Y is not Cys-leu-Ala-Ser-Gly-Ile-Trp (SEQ ID NO:18), Gly-Leu-Leu-Leu-Val-Gly-Ala-Ser-Val-Lu-Gln-Cys-Leu-Ala-Thr-Gly-Asn-Trp-Asn-Ser-Val-Pro-Pro-Glu (SEQ ID NO:19), Leu-Glu-Met-Asn-Tyr-Tyr-Gly-Lys-Gln-Glu-Asn-Trp-Tyr-Ser-Glu-Lys-Lys-Asn-Ser-Arg-Cys (SEQ ID NO:20), Gly-Gly-Ile-Trp-Thr-Trp-Val (SEQ ID NO:28), or Gly-Ile-Trp-Thr-Trp-Val (SEQ ID NO:29), and (2) X-A-B-C-Y does not comprise R¹³-Lys-R¹⁴-Leu-Thr-R⁵-Glu-Ala-Glu-Asn-Trp-R⁶-R⁷ (SEQ ID NO:22), Ala-Glu-Asn-Trp-R⁶-R⁷-R⁸-Glu-Pro-Asn-Asn (SEQ ID NO:23), Ala-Glu-Asn-Trp-R⁶-R⁷-R⁸-Glu-Pro-Asn-Asn-R⁹-R¹⁰ (SEQ ID NO:24), Ala-Glu-Asn-Trp-R⁶-R⁷-R⁸-Glu-Pro-Asn-Asn-R⁹-R¹⁰-R¹¹-R¹²-Glu-Asp (SEQ ID NO:25), Arg-Lys-R¹⁵-R⁸-R¹⁶-R¹⁷-Trp-R¹⁸-Trp-Val-Gly-Thr-R¹³-Lys-R¹⁴-Leu-Thr-R⁵-Glu (SEQ ID NO:26), Asp-Gln-Gln-Leu-Leu-Gly-Ile-Trp-Gly-Cys-Ser (amino acids 11–21 of SEQ ID NO:21), or Arg-Lys-R¹⁵-R⁸-R¹⁶-R¹⁷-Trp-R¹⁸-Trp-Val (SEQ ID NO:27)

wherein R¹³ is Lys, Gln, or Asn; R¹⁴ is Ala, Pro, or Ser; R⁵ is Asn or Glu; R⁶ is Ala or Gly; R⁷ is Asp or Pro; R⁸ is Asn or Gly; R⁹ is Lys or Arg; R¹⁰ is Arg, Gln, or Lys; R¹¹ is Asn or Lys; R¹² is Asn, Asp, or Lys; R¹⁵ is Asn, Val, or Ile; R¹⁶ is Lys, Asn or Gly; R¹⁷ is Thr, Val, or Ile; and R¹⁸ is Thr or Val, and with the proviso that if R¹ is H and R² is OH, then X-A-B-C-Y is not Gly-Gly-D-Ile-D-Trp-D-Thr-D-Trp-D-Val, or Gly-D-Ile-D-Trp-D-Thr-D-Trp-D-Val.

2. The peptide of claim 1 wherein X is selected from the group consisting of Lys-Lys-Ala-Leu-Thr-Asn-Glu-Ala (amino acids 1 to 8 of SEQ ID NO:2), Cys-Lys-Ala-Leu-Thr-Asn-Glu-Ala (amino acids 1 to 8 of SEQ ID NO:3), Ala-Leu-Thr-Asn-Glu-Ala (amino acids 3 to 8 of SEQ ID NO:3), Thr-Asn-Glu-Ala (amino acids 5 to 8 of SEQ ID NO:3), Thr-Asn-Ile-Ala (amino acids 1 to 4 of SEQ ID NO:9), Asn-Glu-Ala, Arg-Lys-Glu-Ala (amino acids 1 to 4 of SEQ ID NO:15), and Ala.

3. The peptide of claim 1 wherein Y is selected from the group consisting of Ala-Asp, Ala-Asp-Asn, Ala-Asp-Asn-Glu-Pro-Asn-Asn-Lys-Arg-Asn-Asn-Glu-Asp (amino acids 12 to 24 of SEQ ID NO:4), Ala-Trp-Asn, Ala-Asp-Asn-Glu (amino acids 12 to 15 of SEQ ID NO:4), Ala-Asp-Asn-Glu-Pro (amino acids 12 to 16 of SEQ ID NO:4), Ala-Asp-Asn-Glu-Pro-Asn-Asn (amino acids 12 to 18 of SEQ ID NO:4), and Thr-Asp-Val.

4. The peptide of claim 1 selected from the group consisting of peptides having the formula:

| | |
|---|---|
| Lys-Lys-Ala-Leu-Thr-Asn-Glu-Ala-Glu-Asn-Trp-Ala-Asp-NH₂ | (Sequence ID No. 1); |
| Lys-Lys-Ala-Leu-Thr-Asn-Glu-Ala-Glu-Asn-Trp-Ala-Asp-Asn-NH₂ | (Sequence ID No. 2); |
| Cys-Lys-Ala-Leu-Thr-Asn-Glu-Asn-Glu-Asn-Trp-Ala-Asp-Asn-NH₂ | (Sequence ID No. 3); |
| Lys-Lys-Ala-Leu-Thr-Asn-Glu-Ala-Glu-Asn-Trp-Ala-Asp-Asn-Glu-Pro-Asn-Asn-Lys-Arg-Asn-Asn-Glu-Asp-NH₂ | (Sequence ID No. 4) |
| Ala-Leu-Thr-Asn-Glu-Ala-Glu-Asn-Trp-Ala-Asp | (Sequence ID No. 5); |
| Thr-Asn-Glu-Ala-Glu-Asn-Trp-Ala-Asp-NH₂ | (Sequence ID No. 7); |
| Thr-Asn-Glu-Ala-Glu-Asn-Trp-Ala-Asp-Asn-NH₂ | (Sequence ID No. 8); |
| Thr-Asn-Ile-Ala-Gly-Ile-Trp-Ala-Trp-Asn-NH₂ | (Sequence ID No. 9); |
| Acetyl-Thr-Asn-Glu-Ala-Glu-Asn-Trp-Ala-Asp-Asn-NH₂ | (Sequence ID No. 8); |
| Thr-Asn-Glu-Ala-Glu-Asn-Trp-Ala-Asp-Asn-Glu-NH₂ | (Sequence ID No. 10); |
| Thr-Asn-Glu-Ala-Glu-Asn-Trp-Ala-Asp-Asn-Glu-Pro-NH₂ | (Sequence ID No. 11); |
| Thr-Asn-Glu-Ala-Glu-Asn-Trp-Ala-Asp-Asn-Glu-Pro-Asn-Asn-NH₂ | (Sequence ID No. 13); |
| Asn-Glu-Ala-Glu-Asn-Trp-Ala-Asp-Asn-NH₂ | (Sequence ID No. 14); |
| Ala-Glu-Asn-Trp-Ala-Asp-Asn-Glu-Pro-Asn-Asn-NH₂ | (Sequence ID No. 16); |
| Ala-Glu-Asn-Trp-Ala-Asp-Asn-Glu-Pro-Asn-Asn-Lys-Arg-Asn-Asn-Glu-Asp-NH₂ | (Sequence ID No. 12) |
| Arg-Lys-Glu-Ala-Glu-Ile-Trp-Thr-Asp-Val-NH₂ | (Sequence ID No. 15); | and pharmaceutically acceptable acid- or base-addition salts thereof.

5. The peptide of claim 1 in combination with a pharmaceutical carrier selected from the group consisting of carriers suitable for parenteral administration, oral administration, topical administration, and controlled release formulations.

6. A method for the preparation of peptides of the formula:

R¹-X-A-B-C-Y-R² or a pharmaceutically acceptable acid- or base-addition salt thereof wherein:

R¹ is a moiety attached to the amine function (NHR¹) of the N-terminal amino acid and R² is the moiety attached to the carbonyl group of the C-terminal amino acid, A is D- or L-glutamic acid or glycine;

B is D- or L-asparagine or D- or L-isoleucine;

C is D- or L-tryptophan;

X and Y are linear chains of from 0 to 16 amino acids;

$R^1$ is H, formyl, lower alkyl, aryl, lower alkanoyl, aroyl, alkyloxycarbonyl or aryloxycarbonyl and $R^2$ is OH, O(lower alkyl), O(aryl), or $NR^3R^4$ where $R^3$ and $R^4$ are independently H, lower alkyl or aryl, with the proviso that if $R^1$ is H, $R^2$ is OH, and X, A, B, C, and Y comprise L-amino acids, then (1) X-A-B-C-Y is not Cys-Leu-Ala-Ser-Gly-Ile-Trp (SEQ ID NO:18), Gly-Leu-Leu-Leu-Val-Gly-Ala-Ser-Val-Leu-Gln-Cys-Leu-Ala-Thr-Gly-Asn-Trp-Asn-Ser-Val-Pro-Pro-Glu (SEQ ID NO:19), Leu-Glu-Met-Asn-Tyr-Tyr-Gly-Lys-Gln-Glu-Asn-Trp-Tyr-Ser-Glu-Lys-Lys-Asn-Ser-Arg-Cys (SEQ ID NO:20), Gly-Gly-Ile-Trp-Thr-Trp-Val (SEQ ID NO:28), or Gly-Ile-Trp-Thr-Trp-Val (SEQ ID NO:29), and (2) X-A-B-C-Y does not comprise $R^{13}$-Lys-$R^{14}$-Leu-Thr-$R^5$-Glu-Ala-Glu-Asn-Trp-$R^6$-$R^7$ (SEQ ID NO:22), Ala-Glu-Asn-Trp-$R^6$-$R^7$-$R^8$-Glu-Pro-Asn-Asn (SEQ ID NO:23), Ala-Glu-Asn-Trp-$R^6$-$R^7$-$R^8$-Glu-Pro-Asn-Asn-$R^9$-$R^{10}$ (SEQ ID NO:24), Ala-Glu-Asn-Trp-$R^6$-$R^7$-$R^8$-Glu-Pro-Asn-Asn-$R^9$-$R^{10}$-$R^{11}$-$R^{12}$-Glu-Asp (SEQ ID NO:25), Arg-Lys-$R^{15}$-$R^8$-$R^{16}$-$R^{17}$-Trp-$R^{18}$-Trp-Val-Gly-Thr-$R^{13}$-Lys-$R^{14}$-Leu-Thr-$R^5$-Glu (SEQ ID NO:26), Asp-Gln-Gln-Leu-Leu-Gly-Ile-Trp-Gly-Cys-Ser (amino acids 11–21 of SEQ ID NO:21), or Arg-Lys-$R^{15}$-$R^8$-$R^{16}$-$R^{17}$-Trp-$R^{18}$-Trp-Val (SEQ ID NO:27)

wherein $R^{13}$ is Lys, Gln, or Asn; $R^{14}$ is Ala, Pro, or Ser; $R^5$ is Asn or Glu; $R^6$ is Ala or Gly; $R^7$ is Asp or Pro; $R^8$ is Asn or Gly; $R^9$ is Lys or Arg; $R^{10}$ is Arg, Gln, or Lys; $R^{11}$ is Asn or Lys; $R^{12}$ is Asn, Asp, or Lys; $R^{15}$ is Asn, Val, or Ile; $R^{16}$ is Lys, Asn or Gly; $R^{17}$ is Thr, Val, or Ile; and $R^{18}$ is Thr or Val, and with the proviso that if $R^1$ is H and $R^2$ is OH, then X-A-B-C-Y is not Gly-Gly-D-Ile-D-Trp-D-Thr-D-Trp-D-Val, or Gly-D-Ile-D-Trp-D-Thr-D-Trp-D-Val, whereby the amino acids are added either singly or in preformed blocks of amino acids to an appropriately functionalized solid support.

7. The method of claim 6 wherein X is selected from the group consisting of Lys-Lys-Ala-Leu-Thr-Asn-Glu-Ala (amino acids 1 to 8 of SEQ ID NO:2), Cys-Lys-Ala-Leu-Thr-Asn-Glu-Ala (amino acids 1 to 8 of SEQ ID NO:3), Ala-Leu-Thr-Asn-Glu-Ala (amino acids 3 to 8 of SEQ ID NO:3), Thr-Asn-Glu-Ala (amino acids 5 to 8 of SEQ ID NO:3), Thr-Asn-Ile-Ala (amino acids 1 to 4 of SEQ ID NO:9), Asn-Glu-Ala, Arg-Lys-Glu-Ala (amino acids 1 to 4 of SEQ ID NO:15) and Ala.

8. The method of claim 6 wherein Y is selected from the group consisting of Ala-Asp, Ala-Asp-Asn, Ala-Asp-Asn-Glu-Pro-Asn-Asn-Lys-Arg-Asn-Asn-Glu-Asp (amino acids 12 to 24 of SEQ ID NO:4), Ala-Trp-Asn, Ala-Asp-Asn-Glu (amino acids 12 to 15 of SEQ ID NO:4), Ala-Asp-Asn-Glu-Pro (amino acids 12 to 16 of SEQ ID NO:4), Ala-Asp-Asn-Glu-Pro-Asn-Asn (amino acids 12 to 18 of SEQ ID NO:4), and Thr-Asp-Val.

9. The method of claim 6 wherein the peptide is selected from the group consisting of peptides having the formula:

```
Lys-Lys-Ala-Leu-Thr-Asn-Glu-Ala-Glu-Asn-Trp-Ala-Asp-NH2;        (Sequence ID No. 1)

Lys-Lys-Ala-Leu-Thr-Asn-Glu-Ala-Glu-Asn-Trp-Ala-Asp-Asn-NH2;   (Sequence ID No. 2)

Cys-Lys-Ala-Leu-Thr-Asn-Glu-Asn-Glu-Asn-Trp-Ala-Asp-Asn-NH2;   (Sequence ID No. 3)

Lys-Lys-Ala-Leu-Thr-Asn-Glu-Ala-Glu-Asn-Trp-Ala-Asp-Asn-        (Sequence ID No. 4)
Glu-Pro-Asn-Asn-Lys-Arg-Asn-Asn-Glu-Asp-NH2;

Ala-Leu-Thr-Asn-Glu-Ala-Glu-Asn-Trp-Ala-Asp;                    (Sequence ID No. 5)

Thr-Asn-Glu-Ala-Glu-Asn-Trp-Ala-Asp-NH2;                        (Sequence ID No. 7)

Thr-Asn-Glu-Ala-Glu-Asn-Trp-Ala-Asp-Asn-NH2;                    (Sequence ID No. 8)

Thr-Asn-Ile-Ala-Gly-Ile-Trp-Ala-Trp-Asn-NH2;                    (Sequence ID No. 9)

Acetyl-Thr-Asn-Glu-Ala-Glu-Asn-Trp-Ala-Asp-Asn-NH2;             (Sequence ID No. 8)

Thr-Asn-Glu-Ala-Glu-Asn-Trp-Ala-Asp-Asn-Glu-NH2;                (Sequence ID No. 10)

Thr-Asn-Glu-Ala-Glu-Asn-Trp-Ala-Asp-Asn-Glu-Pro-NH2;            (Sequence ID No. 11)

Thr-Asn-Glu-Ala-Glu-Asn-Trp-Ala-Asp-Asn-Glu-Pro-Asn-Asn-NH2;   (Sequence ID No. 13)

Asn-Glu-Ala-Glu-Asn-Trp-Ala-Asp-Asn-NH2;                        (Sequence ID No. 14)

Ala-Glu-Asn-Trp-Ala-Asp-Asn-Glu-Pro-Asn-Asn-NH2;                (Sequence ID No. 16)

Ala-Glu-Asn-Trp-Ala-Asp-Asn-Glu-Pro-Asn-Asn-Lys-Arg-Asn-        (Sequence ID No. 12)
Asn-Glu-Asp-NH2;

Arg-Lys-Glu-Ala-Glu-Ile-Trp-Thr-Asp-Val-NH2;                    (Sequence ID No. 15)
``` and pharmaceutically acceptable acid- or base-addition salts thereof.

10. The method for preparation of a peptide of claim 6 whereby the amino acids are assembled either singly or in preformed blocks in solution or suspension by chemical ligation techniques.

11. The method for preparation of a peptide of claim 6 whereby the amino acids are assembled either singly or in preformed blocks in solution or suspension by enzymatic ligation techniques.

12. The method for preparation of a peptide of claim 6 whereby the peptide is produced by inserting nucleic acid encoding the peptide into an expression vector, introducing the expression vector into a host cell, culturing the host cell under conditions that would allow expression of the encoded peptide, and recovering the peptide.

* * * * *